United States Patent
Narisada et al.

(10) Patent No.: US 10,210,735 B2
(45) Date of Patent: Feb. 19, 2019

(54) MONITORING METHOD, INFORMATION PROCESSING APPARATUS, INFORMATION PROCESSING SYSTEM, AND NON-TRANSITORY COMPUTER READABLE MEDIUM

(71) Applicant: Sysmex Corporation, Kobe-shi, Hyogo (JP)

(72) Inventors: Noriyuki Narisada, Kobe (JP); Ryo Yokoyama, Kobe (JP); Miyuki Arai, Kobe (JP); Toshiyuki Sato, Kobe (JP); Shota Hashimoto, Kobe (JP); Yuuki Watanabe, Kobe (JP); Keizo Takamatsu, Fukuoka (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 15/496,572

(22) Filed: Apr. 25, 2017

(65) Prior Publication Data
US 2017/0309148 A1  Oct. 26, 2017

(30) Foreign Application Priority Data
Apr. 26, 2016 (JP) ................................ 2016-088644

(51) Int. Cl.
*G08B 21/02* (2006.01)
*G08B 3/10* (2006.01)
(Continued)

(52) U.S. Cl.
CPC .............. *G08B 21/02* (2013.01); *A61B 5/746* (2013.01); *G06F 19/00* (2013.01); *G08B 27/005* (2013.01);
(Continued)

(58) Field of Classification Search
CPC ....................................................... G08B 21/02
See application file for complete search history.

(56) References Cited

U.S. PATENT DOCUMENTS

2004/0008125 A1* 1/2004 Aratow ................ G06Q 50/265
340/870.07
2006/0036619 A1* 2/2006 Fuerst ................. G06F 19/3443
(Continued)

FOREIGN PATENT DOCUMENTS

JP   2002-279076   9/2002
JP   2003-305010   10/2003
(Continued)

*Primary Examiner* — Joseph H Feild
*Assistant Examiner* — Pameshanand Mahase
(74) *Attorney, Agent, or Firm* — Brinks Gilson & Lione

(57) ABSTRACT

The present invention provides a monitoring method for infectious diseases. The monitoring method includes: obtaining disease information from a plurality of medical facilities 131, 132, 133, and 134; determining the disease occurrence status for each medical facility based on the disease information and a first criterion related to the disease occurrence status at the medical facility; and generating first area alarm information related to the infectious disease status in a first zone based on the disease occurrence status in the medical facilities associated with the first zone divided by a first area division, and a second criterion related to the disease occurrence status in the first zone.

20 Claims, 29 Drawing Sheets

(51) Int. Cl.
- *G08B 25/14* (2006.01)
- *G08B 21/12* (2006.01)
- *G08B 25/10* (2006.01)
- *A61B 5/00* (2006.01)
- *G06F 19/00* (2018.01)
- *G08B 27/00* (2006.01)
- *G16H 50/80* (2018.01)

(52) U.S. Cl.
CPC .............. *G16H 50/80* (2018.01); *Y02A 90/24* (2018.01); *Y02A 90/26* (2018.01)

(56) References Cited

U.S. PATENT DOCUMENTS

| | | | | |
|---|---|---|---|---|
| 2007/0222599 | A1* | 9/2007 | Coveley | A61B 5/1113 340/572.4 |
| 2014/0257047 | A1* | 9/2014 | Sillay | A61B 5/11 600/301 |
| 2016/0132652 | A1* | 5/2016 | Chapman Bates | G06F 19/345 706/11 |

FOREIGN PATENT DOCUMENTS

| | | |
|---|---|---|
| JP | 2005-251027 | 9/2005 |
| JP | 2007-200107 A | 8/2007 |
| JP | 2012-226571 | 11/2012 |
| JP | 2014-186447 | 10/2014 |

\* cited by examiner

Disease table

| Disease type | Monitoring criterion | Facility alarm criterion | Area division | | | | Notification condition | Notification method | | |
|---|---|---|---|---|---|---|---|---|---|---|
| | | | Small area division | Small area alarm criterion | Large area division | Large area alarm criterion | | Facility alarm | Small area alarm | Large area alarm |
| Influenza | Criterion (A) | Criterion (B) | School district | Criterion (C) | Municipality | Criterion (D) | Condition (A) | Method (a) | Method (b) | Method (c) |
| Rubella | ... | ... | OB/GYN vicinity | ... | — | ... | ... | ... | ... | ... |
| Dengue fever | ... | ... | Municipality | ... | Locality | ... | ... | ... | ... | ... |
| Drug resistant bacterial infection | ... | ... | Municipality | ... | Locality | ... | ... | ... | ... | ... |
| ... | ... | ... | ... | ... | ... | ... | ... | ... | ... | ... |

FIG. 1D

| Area division type | Zone definition data by area division ||| 
|---|---|---|---|
| | Zone name | Medical facility | Range of zone |
| School district | School district (A) | Medical facility (a) | — |
| | | Medical facility (b) | |
| | | ⋮ | |
| | School district (B) | Medical facility (c) | — |
| | | Medical facility (d) | |
| | | ⋮ | |
| | ⋮ | ⋮ | — |
| Municipality | Municipality (A) | Medical facility (e) | — |
| | | Medical facility (f) | |
| | | ⋮ | |
| | Municipality (B) | Medical facility (g) | — |
| | | Medical facility (h) | |
| | | ⋮ | |
| | ⋮ | ⋮ | — |
| Prefecture | ⋮ | ⋮ | ⋮ |
| Medical district | ⋮ | ⋮ | ⋮ |
| OB/GYN neighborhood | — | — | 500 m from OB/GYN |
| Nursing home neighborhood | — | — | 500 m from nursing home |
| ⋮ | ⋮ | ⋮ | ⋮ |

FIG. 1E

Medical facility data

| Medical facility | Medical dept | Position information |
|---|---|---|
| Medical facility (a) | Surgery | X |
| Medical facility (b) | OB/GYN | Y |
| ... | ... | ... |

Facility data of non-medical facilities

| Facility (non-medical) | Type | Position information |
|---|---|---|
| School (i) | School | ... |
| School (j) | School | ... |
| Nursing home (k) to (l) | Nursing home | ... |

| Medical facility | Disease type | Exam result | Exam day |
|---|---|---|---|
| ○○General hospital | Influenza | Positive | 2016/4/1 |
| | | Positive | 2016/4/1 |
| | | Positive | 2016/4/1 |
| | | ⋮ | ⋮ |
| | Rubella | Negative | 2016/4/1 |
| | | Negative | 2016/4/2 |
| | | Negative | 2016/4/2 |
| | | ⋮ | ⋮ |

| Medical facility | Disease type | Exam result | Exam day |
|---|---|---|---|
| △△Pediatrics | Influenza | Positive | 2016/4/1 |
| | | Positive | 2016/4/1 |
| | | Negative | 2016/4/1 |
| | | ⋮ | ⋮ |

FIG. 2B

| Medical facility | Patient ID | Bacteria strain | Drug | Day administered | Dosage | Exam day | Exam result |
|---|---|---|---|---|---|---|---|
| ○○General hospital | A | S. aureus | a | 2016/4/1 | 50mg | — | — |
| | | | a | 2016/4/2 | 50mg | — | — |
| | | | a | 2016/4/3 | 50mg | — | — |
| | | | | — | — | 2016/4/4 | Positive |
| | | | a | 2016/4/4 | 50mg | — | — |
| | | | a | 2016/4/5 | 50mg | — | — |
| | | | | | | 2016/4/6 | Negative |
| | | | | ... | ... | ... | ... |
| | B | Tuberculosis | | | | | |

FIG. 2C

MONITORING METHOD, INFORMATION PROCESSING APPARATUS, INFORMATION PROCESSING SYSTEM, AND NON-TRANSITORY COMPUTER READABLE MEDIUM

RELATED APPLICATIONS

This application claims priority from prior Japanese Patent Application No. 2016-088644, filed on Apr. 26, 2016, entitled: "Monitoring Method, Information Processing Apparatus, Information Processing System, And Computer Program", the entire contents of which are incorporated herein by reference.

BACKGROUND OF THE INVENTION

1. Field of the Invention

The present invention relates to a monitoring method, information processing apparatus, information processing system, and computer program.

2. Description of the Related Art

Japanese Patent Application Publication No. 2007-200107 discloses an infectious disease information disclosure system in which a server computer aggregates information on a patient's infectious disease from each of a plurality of medical facilities, creates infection disease disclosure information on a target infectious disease, and transmits infectious disease disclosure information to the computer of the medical facility initiating the request and to residents' personal information terminals of the surrounding area. In this system, a map divided by prefecture or municipality is displayed, the number of occurrences of the target infectious disease is displayed in each zone, and the background color of the zone where the number of occurrences exceeds a predetermined number is displayed in a color different from the other zones.

SUMMARY OF THE INVENTION

However, in the system of Japanese Patent Application Publication No. 2007-200107, since the background color of each zone is determined only depending on whether or not the number of occurrences of patients in the zone exceeds a predetermined number, the number of occurrences of the patients concentrates only on a specific medical facility, and the entire zone where the medical facility is located is displayed as an infectious disease occurrence area. Therefore, it may be difficult to accurately grasp the range in which target infectious diseases are dispersed.

One aspect of the present invention is a monitoring method for infectious diseases. The monitoring method of the embodiment includes acquiring disease information from a plurality of medical facilities. The monitoring method includes determining the disease occurrence status for each medical facility based on the disease information and a first criterion related to the disease occurrence status at the medical facility.

The monitoring method includes generating first area alarm information relating to the disease occurrence status in a first zone. The first zone is an area partitioned by a first area division. The first area alarm information is generated based on the disease occurrence status in the medical facility associated with the first zone and a second criterion related to the disease occurrence status in the first zone.

Another aspect of the present invention is an information processing apparatus for monitoring infectious diseases. An information processing apparatus according to an embodiment includes an information processing part. The information processing part executes a first process of determining the disease occurrence status for each medical facility based on the disease information acquired from a plurality of medical facilities and the first criterion concerning the disease occurrence status at the medical facility. The information processing part executes a second process to generate first area alarm information related to the infectious disease occurrence status in a first zone based on the disease occurrence status in the medical facility associated with the first zone partitioned by the first area division and a second criterion related to the disease occurrence status in the first zone.

Another aspect of the present invention is an information processing system for monitoring infectious diseases. The system of the embodiment includes a first information processing apparatus and a second information processing apparatus. The first information processing apparatus executes a first process of determining the disease occurrence status for each medical facility based on the disease information acquired from a plurality of medical facilities and a first criterion related to the disease occurrence status at the medical facility. The information processing apparatus executes a second process to generate first area alarm information related to the infectious disease occurrence status in the first zone based on the disease occurrence status in the medical facility associated with the first zone partitioned by the first area division and a second criterion related to the disease occurrence status in the first zone.

The second information processing apparatus is an information processing apparatus separate from the first information processing apparatus. The second information processing apparatus executes a process of communicating the first area alarm information provided from the first information processing apparatus by a notification method corresponding to the type of the first area partition.

Yet another aspect of the invention is a computer program to perform computer-executable processes. The computer program enables the computer to function as an information processing apparatus. The computer program is stored, for example, in a computer readable storage medium.

According to the invention, since the alarm information is generated for the zone associated with the medical facility where the infectious disease occurs, it is possible to more accurately grasp the range in which the infectious disease is dispersing.

BRIEF DESCRIPTION OF THE DRAWINGS

FIG. 1D is a structural diagram of a disease table;

FIG. 1E is a structural diagram of zone setting data by area division;

FIG. 1F is a structural diagram of medical facility data;

FIG. 1G shows the structure of facility data other than medical facilities;

FIG. 2B is a diagram showing an example of aggregation information;

FIG. 2C is a diagram showing an example of aggregation information;

DETAILED DESCRIPTION OF THE PREFERRED EMBODIMENTS

1. Information Processing Apparatus

Figure 1A:
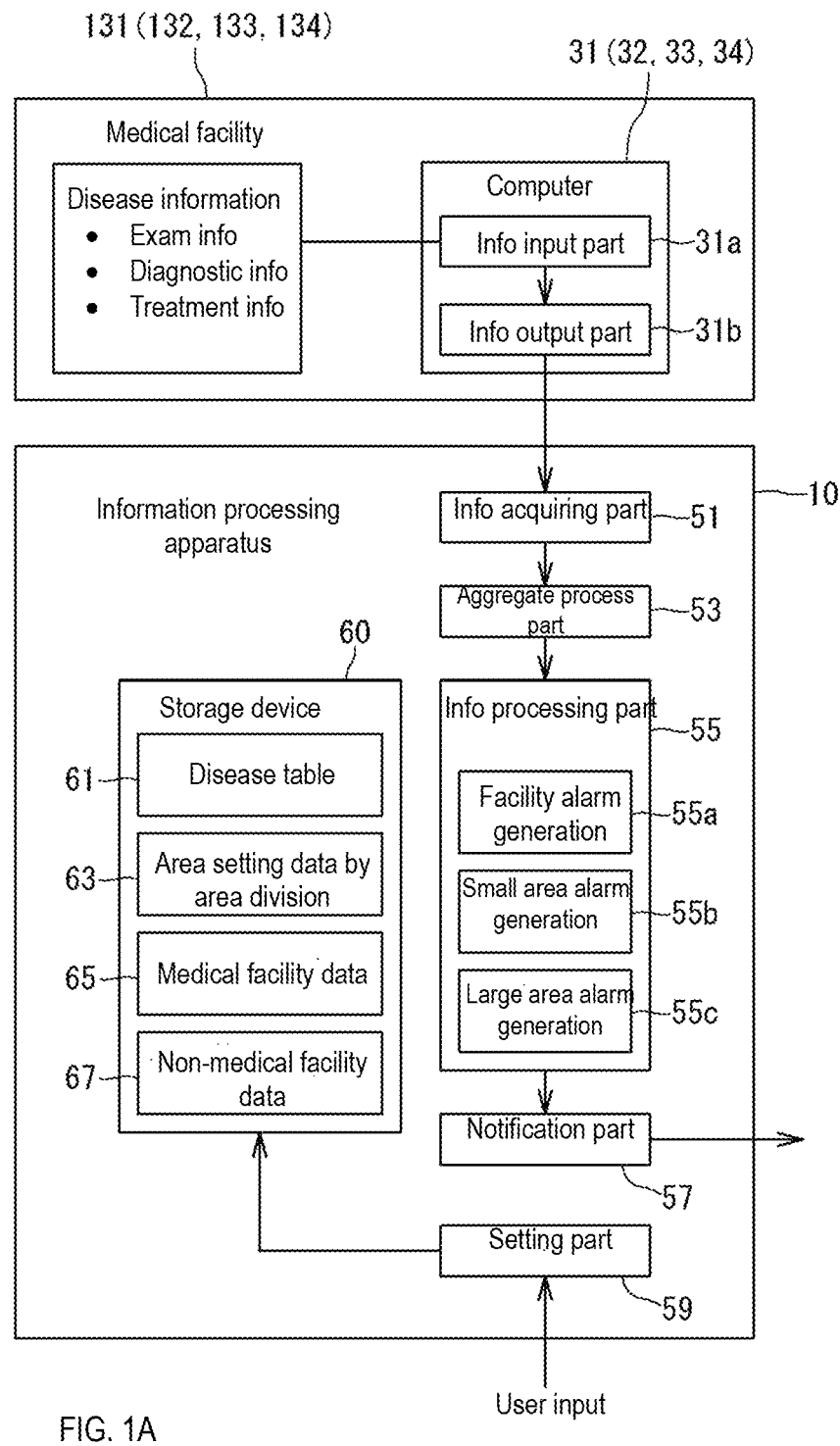
FIG. 1A is a block diagram of an information processing apparatus and a medical facility computer.
Figure 1B:
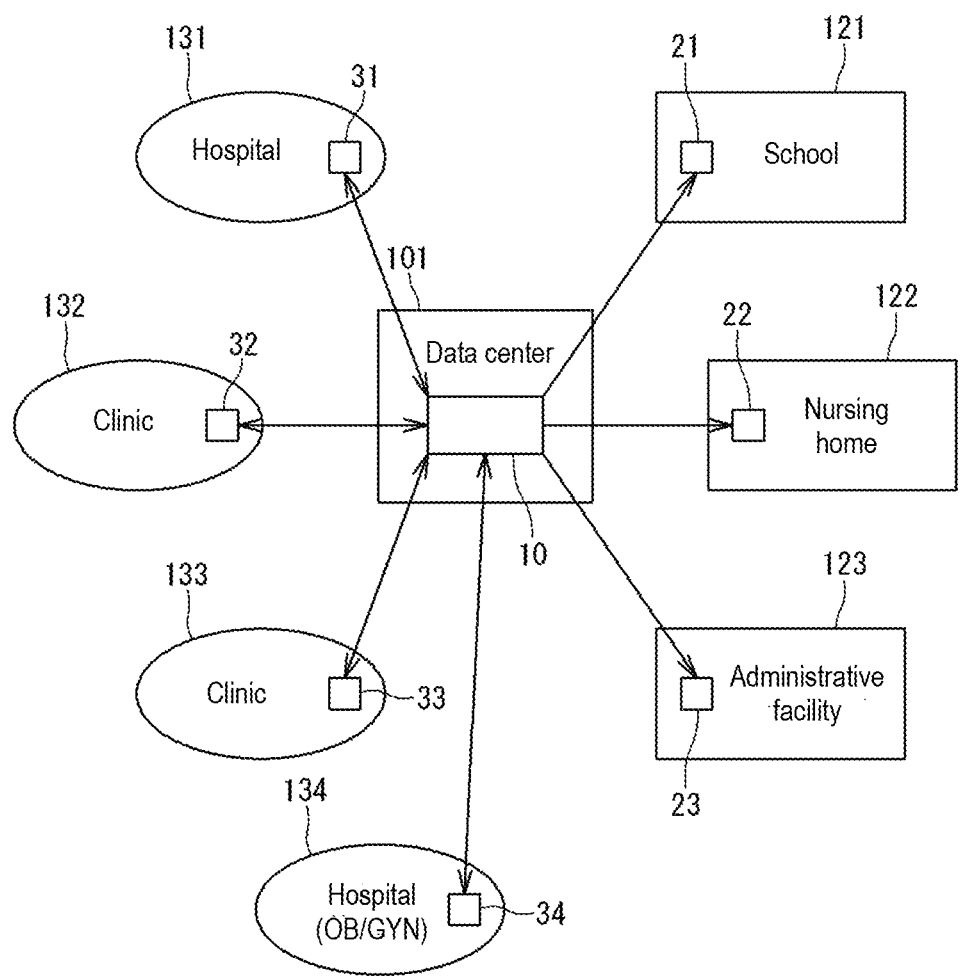
FIG. 1B is a configuration diagram of a network system including an information processing apparatus.

The information processing apparatus 10 shown in FIG. 1A monitors disease information acquired from the medical facilities 131, 132, 133, and 134. As shown in FIG. 1B, the information processing apparatus 10, for example, is installed in a data center. The information processing apparatus 10 is connected to computers 31, 32, 33, 34 installed in a plurality of medical facilities 131, 132, 133, 134 via a computer network. The information processing apparatus 10 is connected to computers 21, 22, 23 installed in a plurality of non-medical facilities 121, 122, 123 via a computer network.

Medical facilities 131, 132, 133, and 133 are facilities for examining, diagnosing, or treating diseases, for example, hospitals or clinics. Facilities other than medical facilities are, for example, such as school 121, nursing home 122, and administrative organizations 123 such as a public health center and the like.

As shown in FIG. 1A, the computer 31 of the medical facility 131 functions as an information input part 31a for inputting disease information, and an information output part 31b for outputting disease information to the information processing apparatus 10. The same applies to the computers 32, 33, 34 of the other medical facilities 132, 133, 134.

Each medical facility performs at least one among examination, diagnosis and treatment to generate disease information. The examination, diagnosis or treatment may be carried out by a healthcare worker or may be carried out by an analytical instrument.

The disease information is information related to the disease and is used for determining the occurrence status of the disease. The disease information is, for example, examination information indicating an examination result, diagnostic information indicating a diagnosis result, or treatment information indicating a treatment result. The disease information includes, for example, patient name, patient ID, disease type, result (examination result/diagnosis result/treatment result etc.), and date (examination date/diagnosis date/treatment day and the like). For the purpose of determining the disease occurrence status which is described later, the disease information preferably includes at least the disease type, the result, and the date. The patient ID may be a medical or similar ID for identifying an individual in the medical field.

The disease is, for example, an infectious disease. Infectious disease types include, for example, influenza, rubella, measles, infectious gastroenteritis, viral hepatitis, mycoplasma pneumonia, RS viral infection, bacterial meningitis, varicella (chicken pox), dengue fever, and Zika fever.

The information input part 31a accepts input of the generated disease information. The information output part 31b transmits the input disease information to the information processing apparatus 10 of the data center 101 in real time. The computer 31 transmits disease information to the information processing apparatus 10 regardless of whether the result indicated by the disease information is positive or negative.

The information processing apparatus 10 acquires disease information from the computers 31, 32, 33, 34 of the medical facility via the network. The information processing apparatus 10 functions as a server that acquires information from a medical facility and provides information such as alarm information indicating facilities and areas where infectious diseases have spread, to medical facilities and facilities other than medical facilities. The information processing apparatus 10 is a computer that executes a computer program, and includes a CPU, a storage device, and the like. The information processing apparatus 10 is also provided with an input device such as a mouse, a keyboard and the like, which are used for data entry work, selection work by the user. The computer program is stored in the storage device of the computer. The computer reads and executes the computer program stored in the storage device and realizes functions for acquiring and providing information.

As shown in FIG. 1A, the information processing apparatus 10 functions as an information acquiring part 51. The information acquiring part 51 acquires disease information output from each medical facility. Since computers of a plurality of medical facilities are connected to the information processing apparatus 10, disease information from a plurality of medical facilities is consolidated in the information processing apparatus 10. The information acquiring part 10 stores the obtained disease information in the storage device 60.

The information processing apparatus 10 functions as an aggregate processing part 53. The aggregate processing part 53 performs a counting process on the disease information stored in the storage device 60. It is preferable that the counting process includes at least processing for aggregating disease information according to the disease type for each medical facility. The counting process may include, for example, a process of obtaining an average value of disease information or a statistical process of obtaining a standard deviation. Hereinafter, the disease information subjected to the counting process is also referred to as summing information. The aggregate processing part 53 stores the aggregation information in the storage device 60. Since disease information is transmitted in real time, summary information also changes from moment to moment.

The information processing apparatus 10 functions as an information processing part 55 that generates alarm information. The information processing part 55 performs processing based on the summing information stored in the storage device 60. The information processing part 55 monitors aggregation information that changes from moment to moment and generates alarm information as necessary. The alarm information generated by the information processing part 55 is, for example, facility alarm information, small area alarm information, or large area alarm information to be described later.

The information processing apparatus 10 functions as a notification part 57. The notification part 53 performs a process of communicating the alarm information. The notification method of the alarm information follows the method specified by the information processing part 55. The notification destination of the alarm information may be the computers 31, 32, 33, 34 of the medical facilities 131, 132, 133, 134, or the computers 21, 22, 23, 24 of the non-medical facilities 121, 122, 123, 124.

The information processing apparatus 10 functions as a setting part 57. The setting part 59 sets various data 61, 63, 65, 67 stored in the storage device 60 based on user input. The user is, for example, a system administrator in the center 101. The setting of the data 61, 63, 65, 67 is performed before the operation of the information processing apparatus 10 starts. Even after starting the operation of the information processing apparatus 10, it is possible to flexibly change the monitoring method and the notification method of the alarm information by appropriately changing the data 61, 63, 65, 67.

Figure 1C:
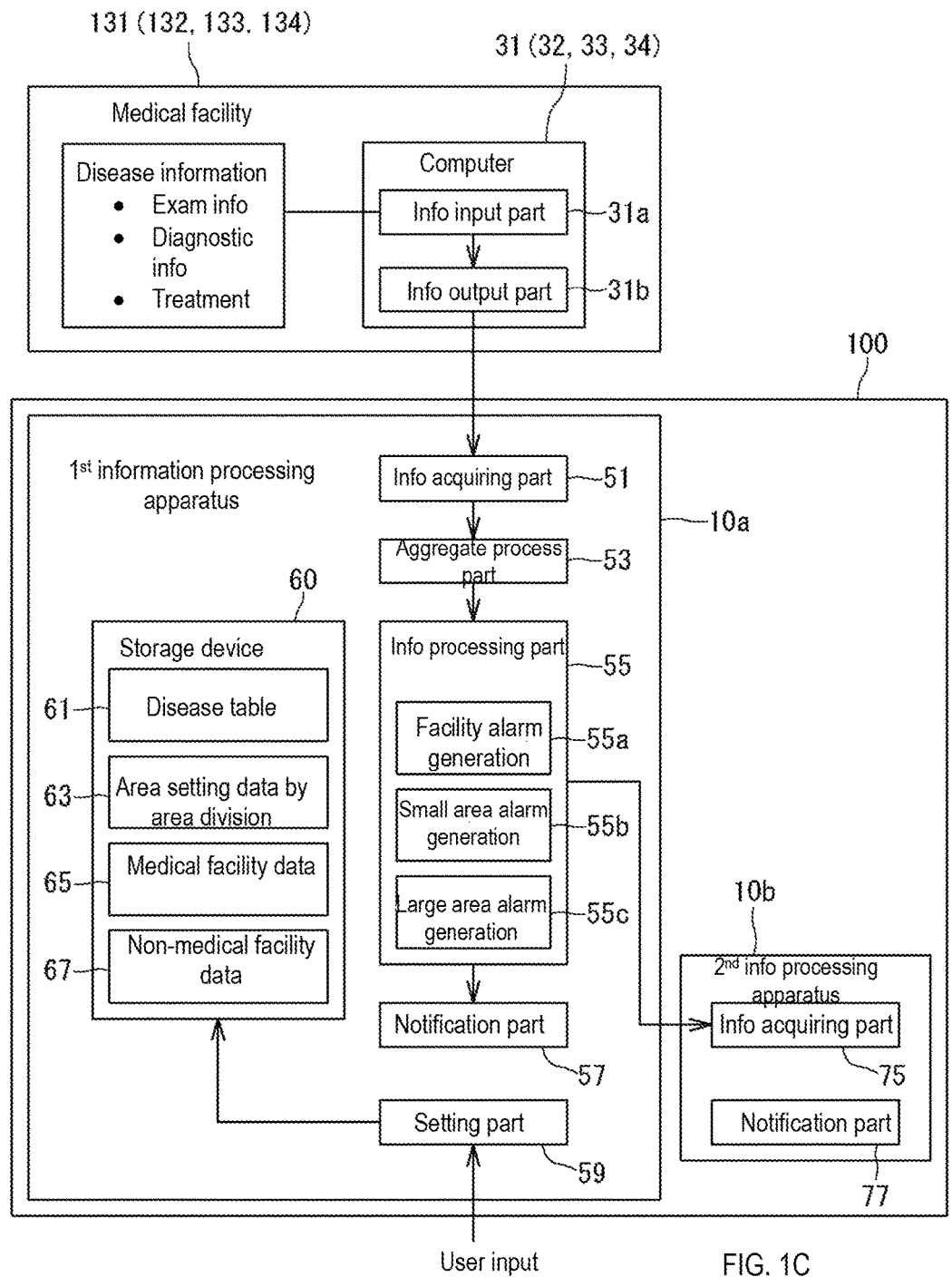
FIG. 1C is a block diagram showing a modification of the information processing apparatus.

FIG. 1C shows an example in which the information processing system 100 including the first information processing apparatus 10a and the second information processing apparatus 10b is installed in the data center 101. The first information processing apparatus 10a functions as a server that acquires information from a medical facility and provides information such as alarm information to the medical facility. The second information processing apparatus 10b functions as a server that provides alarm information to facilities other than medical facilities. Each information processing apparatus 10a and 10b is a computer that executes a computer program. The computer program is stored in the storage device of the computer. The computer reads and executes the computer program stored in the storage device and realizes functions for acquiring and providing information.

Medical-related data including disease information often includes information requiring careful handling of personal information such as the patient's name. In the information processing system 100 of the embodiment, in order to protect personal information and the like, a notification part 57 for notifying medical facilities and a notification part 77 for notifying facilities other than medical facilities are separate.

The functions of the information acquiring part 51, the aggregate processing part 53 and the information processing part 55 of the first information processing apparatus 10a have the same functions as those of the parts 51, 53, 55 of the information processing apparatus 10 of FIG. 1A. However, the information processing part 55 of the first information processing apparatus 10a provides, to the notification part 57, alarm information to be communicated to the medical facility out of the generated alarm information. The alarm information communicated to the medical facility may include personal information. The notification part 57 notifies the medical facility of the alarm information.

The information processing part 55 provides the alarm information to the second information processing apparatus 10b. The alarm information provided to second information processing apparatus 10b is alarm information to be communicated to facilities other than medical facilities. After removing the personal information included in the alarm information, the information processing part 55 gives the alarm information to the information acquiring part 75. The information acquiring part 75 obtains the alarm information. The acquired alarm information is sent to facilities 121, 122, 123, 124, which are facilities other than medical facilities. The second information processing apparatus 10b notifies the facilities other than the medical facilities of the alarm information, but the personal information is protected since the personal information is not handled. The following description is based on the information processing apparatus 10 of FIG. 1A.

2. Disease Information Acquisition and Aggregation Process

Figure 2A:
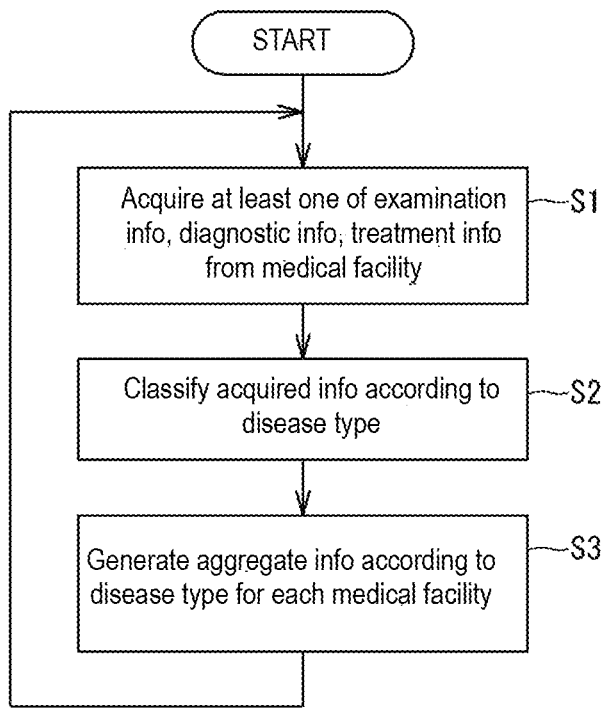
FIG. 2A is a flowchart of disease information acquisition and aggregate processing.

FIG. 2A shows a processing procedure from acquisition of disease information to generation of summary information. The process of FIG. 2A is executed by the information processing apparatus 10. In step S1, the information acquiring part 51 acquires disease information from the computer of the medical facility. Acquisition of information at this point is made irrespective of the result of examination, diagnosis or treatment. In step S2, the aggregate processing part 53 classifies the disease information according to the disease type included in the disease information. In step S3, the aggregate processing part 53 generates aggregation information corresponding to the disease type for each medical facility. In step S3, a statistical process may be performed to obtain an average value, a standard deviation, and the like.

The aggregate information is, for example, information classified as shown in FIG. 2B. In FIG. 2B, the aggregate information includes the medical facility, the disease type, the examination result, the examination date. In FIG. 2B, disease information is collected for each medical facility according to the disease type. The aggregate information is, for example, information classified as shown in FIG. 2B. In FIG. 2C, the aggregate information includes the medical facility, the patient ID, the bacteria strain, the medication, the medication day, the dosage, the examination date, and the examination result. In FIG. 2C, aggregate information is collected for each medical facility in accordance with the bacterial strain. Because infectious diseases can be classified by pathogens, bacterial species indicate the type of infectious disease.

3. Medical Facility Alarm

Figure 3A:
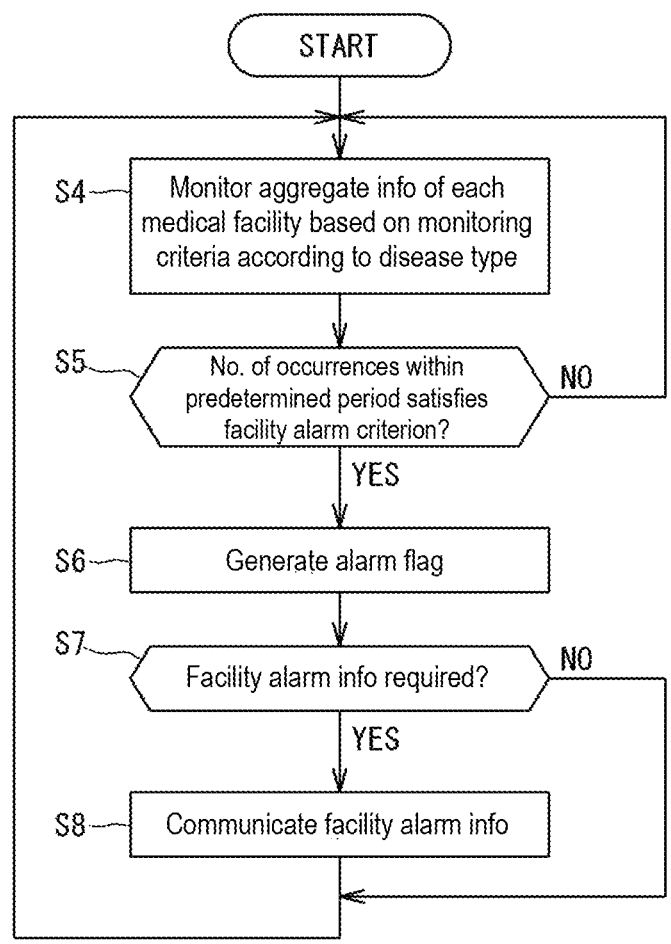
FIG. 3A is a flowchart of the facility alarm generation process.

FIG. 3A shows the facility alarm generation process 55a. The facility alarm generation process 55a is a process of generating alarm information for each medical facility. Alarm information for each medical facility is referred to as facility alarm information.

In step S4, the information processing unit 55 monitors the aggregate information which is the disease information subjected to the aggregation process. This monitoring is performed based on criteria for monitoring the occurrence status of the disease based on the disease information subjected to the aggregation process. This standard is referred to as a monitoring criterion. The monitoring criterion is set in advance in the storage device 60 according to the disease type.

As shown in FIG. 1D, the monitoring criterion 61*b* is set in association with the disease type 61*a* in the disease table 61 which shows the setting information for each disease type. The monitoring criterion 61*b* is, for example, "to obtain the number of occurrences of disease X occurring in the most recent date Y in each medical facility." The number of occurrences of the disease is, for example, a number determined to be positive, and the number of measurements exceeding a threshold value. The monitoring of the disease occurrence status is performed for each medical facility.

In step S5, the information processing part 55 determines whether the disease occurrence status for each medical facility satisfies the determination criteria. This criterion is called the facility alarm criterion. The facility alarm criterion is used to determine whether the disease occurrence status of the medical facility is such that an alarm is necessary. The facility alarm criterion is set in advance in the storage device 60 according to the disease type.

As shown in FIG. 1D, the facility alarm criterion 61*c* is set in association with the disease type 61*a* in the disease table 61. The facility alarm criterion is, for example, a reference value for the number of diseases occurring within a predetermined period.

If it is determined in step S5 that the disease occurrence status for each medical facility satisfies the facility alarm criterion, then in step S6, the information processing unit 55 generates an alarm flag for the medical facility whose disease occurrence status satisfies the facility alarm criterion. The alarm flag indicates that the disease occurrence status meets the facility alarm criterion.

In step S7, the information processing part 55 determines the necessity of notification of facility alarm information based on the disease occurrence status of each medical facility. The facility alarm information is information indicating the medical facility where the occurrence status of the disease meets the facility alarm criterion. That is, the facility alarm information is information indicating that infectious disease is spreading within the facility. The facility alarm information is generated by the information processing part 55 based on the alarm flag. The necessity of notification of the facility alarm information is determined on the basis of the notification condition previously set in the storage device 60.

As shown in FIG. 1D, the notification condition 61*e* is set in association with the disease type 61*a* in the disease table 61. The notification condition 61*e* indicates a condition for communicating facility alarm information. For example, the necessity of notification of facility alarm information is set as the notification condition 61*e*.

When it is determined that the notification of the facility alarm information is necessary based on the notification condition 61*e*, the notification part 57 communicates the facility alarm information in step S8. The facility alarm information is communicated by the notifying method set in advance in the storage device 60. As shown in FIG. 1D, the notification method 61*f* is set in association with the disease type 61*a* in the disease table 61. The notification method 61*f* includes, in addition to a facility alarm information notification method 168, a small area alarm information notification method 169 (to be described later), and a large area alarm information notification method 170. The notification methods 168, 169, and 170 are set for each type of alarm information.

Examples of items set as the notification method 168 include notification means, types of notifications, notification destinations. The notifying means is, for example, distribution by e-mail, display on the Web, distribution by SNS. The type of notification is, for example, notification as a notification/report, notification by display, notification accompanied by a warning report, or notification accompanying an alarm. The notification destination is, for example, an administrative institution such as a medical facility, a school, a nursing home, a care house, a public health center. By including facilities other than medical facilities as the notification destination, monitoring results can be effectively utilized even at non-medical facilities. Note that the items set as the notification methods 169 and 170 also are the same as the notification method 168.

In the embodiment, the notification method 168 of the facility alarm information can be set regardless of the medical facility where the alarm occurred. Therefore, it is possible to flexibly set the notification destination for which the facility alarm information is necessary.

4. Small Area Alarm

Figure 3B:
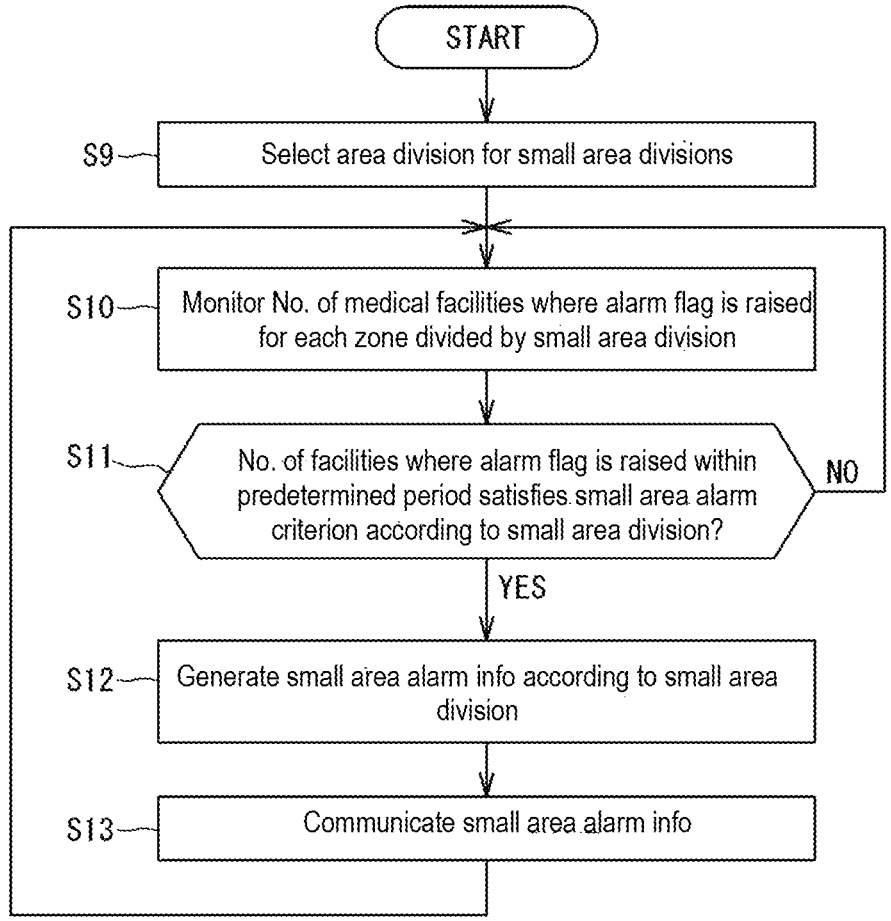
FIG. 3B is a flowchart of the small area alarm generation process.

FIG. 3B shows the small area alarm generation process 55*b*. The small area alarm generating process 55*b* is a process of generating alarm information for each small area divided by a small area division. The alarm information of each of small area is referred to as small area alarm information.

In step S9, the information processing part 55 selects an area division to be small area division. Area division means an area divided within the jurisdictional area by the information processing apparatus 10 according to a certain criterion. In the present embodiment, plural types of area divisions having different criteria for division of areas are preset. The system flexibility is high since it is possible to select a small area division from a plurality of types of area division. In the present embodiment, it is also possible to change the plurality of types of area divisions themselves by changing the setting of the area setting data 63 by area division.

For example, if the jurisdictional area is one prefecture, the area within the prefecture can be divided, for example, by school district units, or it can be divided by municipality units: 28/5000. Here, the area division is expressed by the name of the unit of the area to be divided. Besides school districts, and municipality, prefectures, districts, and medical districts may be used as area divisions. The more types of area divisions that are set, the greater the options for small area division, and the greater the flexibility of the system.

Here, municipalities and prefectures are the type of area division based on administrative districts in Japan, and the administrative division on which the area division is based may be appropriately changed depending on the country. For example, in the case where the present invention is implemented in the United States, a state, a district, a county, an independent city may be used as an area division based on the administrative division. In the case where the present invention is implemented in China, ministries, autonomous regions, direct jurisdictions, special administrative districts, jurisdictions and the like may be used. A district, for example, is a range including a plurality of prefectures. The medical zone is a unit set for medical provision, and may be a municipal unit, an area composed of a plurality of municipalities, or a prefecture unit.

The area division also may be a specific facility neighborhood area unit. The specific facility is, for example, obstetrics and gynecology or a nursing home. For a specific facility, facility users preferably include infection-vulnerable persons. The infection-vulnerable person is, for example, a person who is highly likely to be infected, a person who is highly likely to become seriously ill when infected, or a person who is likely to be affected by infection. Infection-vulnerable persons are, for example, elderly persons, pregnant women, and children.

The small area division is selected based on a preset plurality of kinds of area divisions, for example, based on the disease type. The selection of the small area division according to disease type is performed using, for example, the disease table 61 shown in FIG. 1D.

In the disease table 61 shown in FIG. 1D, the disease type 61a and the area division 61d are associated with each other. The area division 61 includes a small area division 161 and a large area division 163. The large area division 163 is used for generating large area alarm information to be described later. The zone divided by the large area division is preferably wider than the area divided by the small area division.

In FIG. 1D, for example, the disease category 61a, "influenza", is associated with a school district as a small area division 161, and a municipality is associated as a large area division 163. If the disease to be monitored is influenza, the information processing part 55 refers to the disease table 61, selects a school district as a small area division, and selects a municipality as a large area division. The same applies to other diseases (rubella, dengue, drug resistant infection).

In step S10, the information processing part 55 monitors alarm flags indicating the disease occurrence status in the medical facilities. In this monitoring, the number of medical facilities for which the alarm flag is set is obtained for each zone divided by the small area division for the disease targeted for monitoring. The zone divided by the selected area division selected as the small area division is called a small area.

As shown in FIG. 1E, the correspondence between the zone and the medical facility is set in advance in the storage device 60 as area setting data 63 by area division. The area setting data 63 includes an area division type 63a and area definition data 63b. The area definition data 63 includes the zone name 63c, the medical facility 63d associated with the zone name 63c, and the zone range 63e of the zone associated with the zone name 63c. In FIG. 1E, a plurality of zones 63c, such as school district (A), school district (B) and the like under "school district" are set in the area division 63a "school district." One or more medical facilities 63d such as medical facilities (a), (b), (c), (d) and the like are associated with each school district (A), (B) as a zone. The information processing part 55 recognizes the medical facility 63d associated with the zone name 63c as a medical facility located in the zone.

In the embodiment, in the case of the area division based on the school district or the administrative division, as shown in FIG. 1E, the zone is defined by the medical facility 63d belonging to that area. On the other hand, when the area division is "a specific facility neighboring area" such as "neighborhood of obstetrics and gynecology" or "neighborhood of senior citizen" as shown in FIG. 1E, the area is defined by zone range 63e. A range of zones is defined, for example, as a distance from a specific facility. The area near the Obstetrics and Gynecology Department, for example, is defined as "within 500 meters from the Obstetrics and Gynecology Department", and the area in the vicinity of the elderly home is defined as "within 500 m from the seniors' home." The information processing part 55 refers to the location information of the specific facility and the location information of the medical facility and recognizes the medical facility corresponding to the definition in the zone range 63e as a medical facility located within the zone.

The position information of the medical facility is set in the storage device 60 in advance as medical facility data 65 shown in FIG. 1F. The medical facility data 65 includes a medical facility 65a, a medical department 65b, and position information 65c. The medical department 65b shows the department of the medical facility 65a, and the position information 65c shows the position of the medical facility 65a.

Position information of facilities other than medical facilities is set in the storage device 60 in advance as the facility data 67 shown in FIG. 1G. The facility data 67 has a facility 67a that is a non-medical facility, a type 67b, and position information 67c. The type 67 is the type of the facility 67a, for example, a nursing home or a school. The position information 67c indicates the position of the facility 67a.

Whether the medical institution is a specific facility (obstetrics and gynecology department, senior citizen home or the like) is recognized based on the clinical department 65b or the type 67b.

In step S10, if the small area is, for example, a school district, the number of medical facilities with an alarm flag set is monitored for each school district. For example, if the small area is in the vicinity of the Obstetrics and Gynecology Department, the number of medical institutions with alarm flags set up is monitored within 500 m from the obstetrics and gynecology department for each medical facility with obstetrics and gynecology.

In step 11, the information processing part 55 determines whether the disease occurrence status for each small area divided by the small area division satisfies the determination criterion. This criterion is referred to as a small area alarm criterion. The small area alarm criterion is used to determine whether the disease occurrence status in the small area is a situation requiring an alarm. The small area alarm criterion is set in advance in the storage device 60 according to the disease type.

As shown in FIG. 1D, the small area alarm criterion 162 is set in association with the small area division 161 for each disease type 61a. The small area alarm criterion 162 is, for example, a reference value for the number of medical facilities in a small area where an alarm flag is set within a predetermined period. Since the small area alarm criterion 162 is associated with the small area division 161 and is set for each small area division, it is a criterion corresponding to the type of the small area division 161.

If it is determined in step S11 that the disease occurrence status for each small area satisfies the small area alarm criterion, then in step S12 the information processing part 55 determines whether the small area where the disease occurrence status satisfies the small area alarm criterion and generates small area alarm information. Small area alarm information is information indicating that infectious disease is spreading in small areas and is useful for prevention and countermeasures of disease in the corresponding small areas.

In step S13, the notification part 57 communicates the small area alarm information. The notification of the small area alarm information is performed according to a preset notification method. As shown in FIG. 1D, the notification method 169 for small area alarm information is associated with not only the disease type 61*a* but also the small area division 161 in the disease table 61. Since the notification method 169 is set for each small area division 161, the notification method 169 is a notification method according to the type of the small area division 161. The items set as the notification method 169 is the same as the notification method 168.

In the embodiment, since the notification method 169 for small area alarm information can be set separately from the small area division 161, the setting of the notification destination set in the notification method 169 can be performed irrespective of the zone by the small area division 161. Therefore, it is possible to flexibly set the notification destination for which the small area alarm information is necessary.

5. Large Area Alarm

Figure 3C:
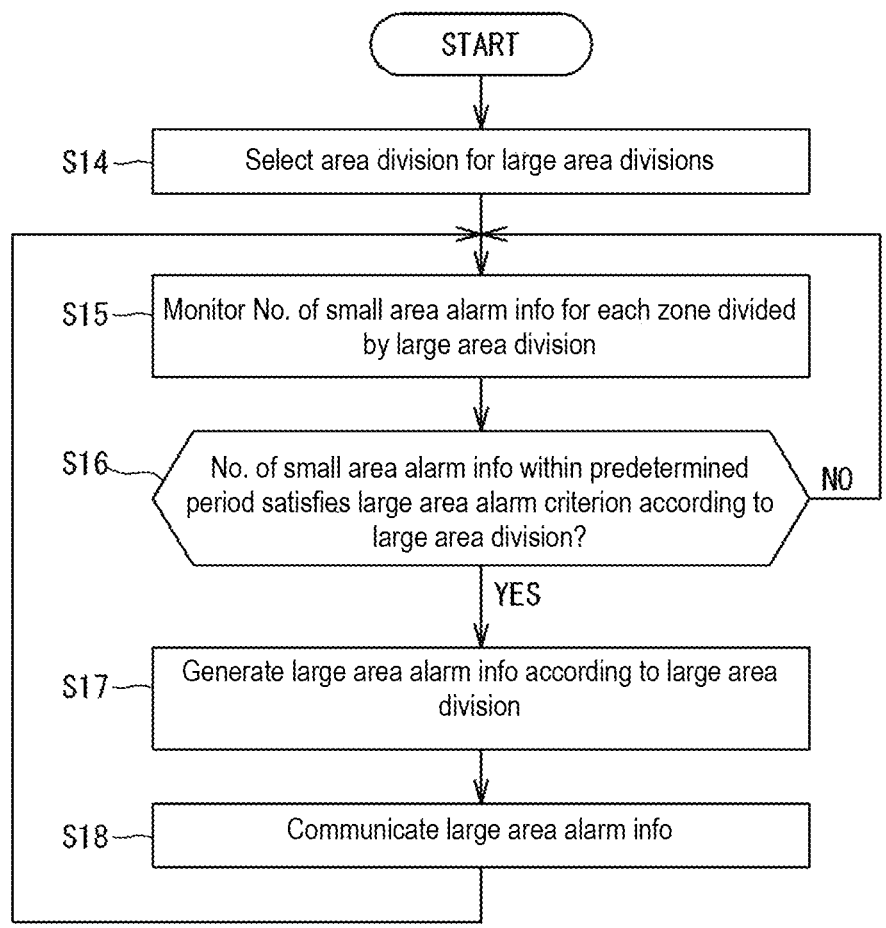
FIG. 3C is a flowchart of the large area alarm generation process.

FIG. 3C shows the large area alarm generating process 55*c*. The large area alarm generating process 55*c* is a process of generating alarm information for each large area divided by a large area division. The alarm information of each of large area is referred to as large area alarm information.

In step S14, the information processing part 55 selects an area division to be large area division. The large area division is selected based on a plurality of preset kinds of area divisions, for example, based on the disease type. Selection of the large area division based on the disease type is performed, for example, using the disease table 61. The large area division is selected as an area division type different from that of the small area division. The system flexibility is high since it is possible to select a large area division from a plurality of types of area division.

In FIG. 1D, for example, municipalities are associated with the disease category 61*a*, "influenza", as the large area division 163. If the disease to be monitored is influenza, the information processing part 55 refers to the table 61 and selects a municipality as a large area division.

In step S15, the information processing part 55 monitors the small area alarm information that indicates the disease occurrence status in the small area. In this monitoring, the number of small area alarm information is obtained for each zone divided by the large area division for the target disease being monitored. The zone divided by the selected area division selected as the large area division is referred as a large area.

For example, a municipality may include multiple school districts. In the case where the small area is a school district and the large area is the municipality, the number of small area alarm information in that city becomes two when the small area alarm information occurs in two school districts in that city. Note that in each disease type, one or a plurality of small areas corresponding to the large area are correlated.

In step S16, the information processing part 55 determines whether the disease occurrence status for each large area divided by the large area division satisfies the determination criterion. This criterion is referred to as a large area alarm criterion. The large area alarm criterion is used to determine whether the disease occurrence status in the large area is a situation requiring an alarm. The large area alarm criterion is set in advance in the storage device 60 according to the disease type.

As shown in FIG. 1D, the large area alarm criterion 164 is set in association with the large area division 163 for each disease type 61*a*. The large area alarm criterion 164 is, for example, a reference value of the number of small area alarm information in the large area that have occurred within a predetermined period. Since the small area alarm criterion 162 is associated with the large area division 163 and is set for each large area division, it is a criterion corresponding to the type of the large area division 163.

If it is determined in step S16 that the disease occurrence status for each large area satisfies the large area alarm criterion, then in step S17 the information processing part 55 determines that the large area where the disease occurrence status satisfies the large area alarm criterion and generates alarm large area information. large area alarm information is information indicating that infectious disease is spreading in large areas and is useful for prevention and countermeasures of disease in the corresponding large areas.

In step S18, the notification part 57 communicates the large area alarm information. The notification of the large area alarm information is performed according to a preset notification method. As shown in FIG. 1D, the notification method 170 for large area alarm information is associated with not only the disease type 61*a* but also the large area division 163 in the disease table 61. Since the notification method 170 is set for each large area division 163, the notification method 170 is a notification method according to the type of the large area division 163. The items set as the notification method 170 are the same as the notification method 168.

In the embodiment, since the notification method 170 for large area alarm information can be set separately from the large area division 163, the setting of the notification destination set in the notification method 170 can be performed irrespective of the zone by the large area division 163. Therefore, it is possible to flexibly set the notification destination for which the large area alarm information is necessary.

6. Monitoring a Plurality of Diseases

The information processing part 55 monitors a plurality of diseases in parallel and generates alarm information for each disease. Below, a specific example of the alarm information generation process will be described taking influenza, rubella, dengue fever, and drug resistant bacterial infection as examples.

6.1 Influenza 6.1.1 Influenza Facility Alarm

Figure 4A:
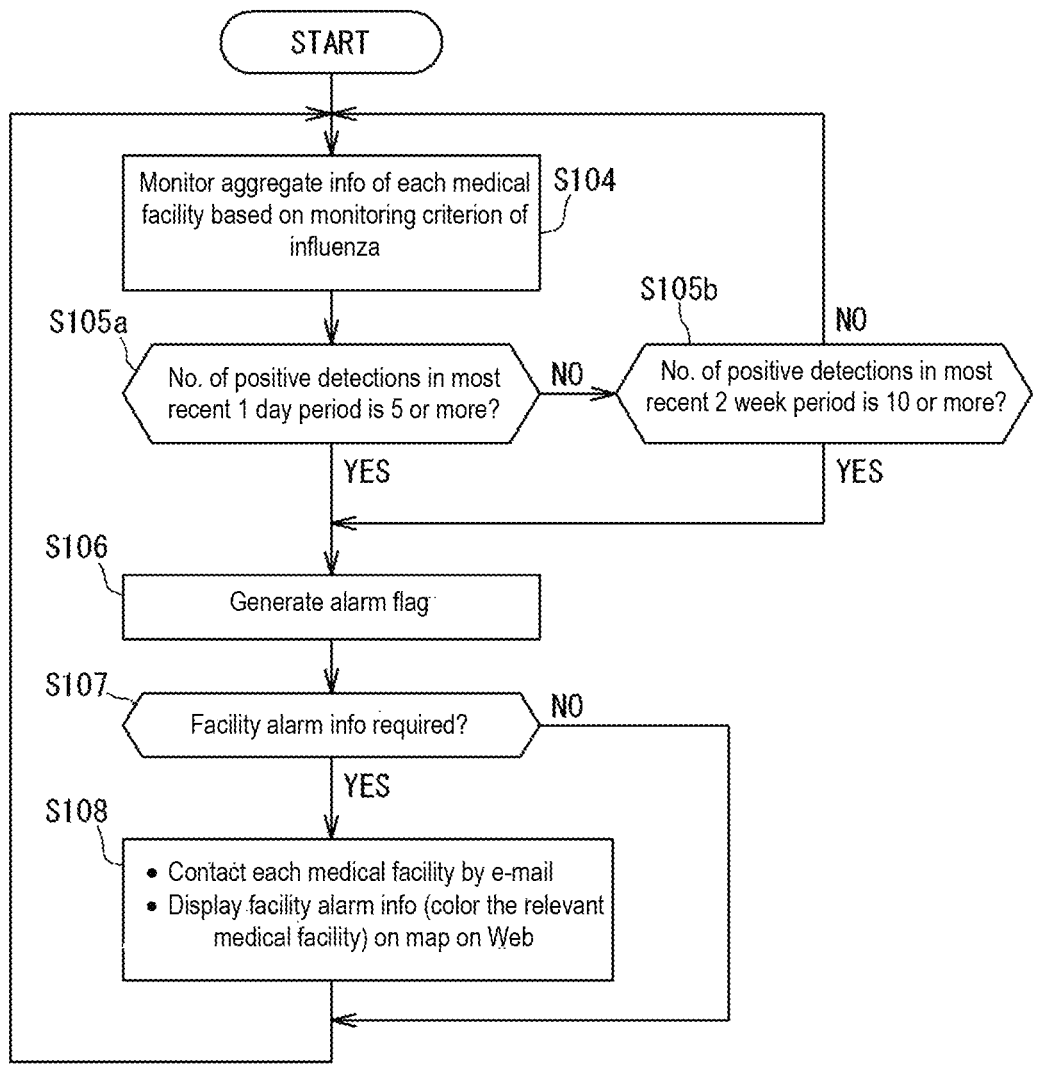
FIG. 4A is a flowchart of the facility alarm generation process for influenza.

FIG. 4A shows the facility alarm generation process 55*a* for influenza. Step S104 corresponds to step S4 in FIG. 3A. Based on the fact that the disease type to be monitored is influenza, the information processing part 55 refers to the disease table 61 of FIG. 1D and acquires the criterion (A) as the monitor criterion 61*b* corresponding to the disease type 61*a*, "influenza." In step S104, the information processing part 55 monitors the aggregation information of each medical facility based on the acquired criterion (A). For example, criterion (A) is "to obtain the number of cases where detection is positive in influenza tests in the most recent period of Y days in each medical facility."

Steps S105*a* and S105*b* correspond to step S5 of FIG. 3A. Based on the fact that the disease type is influenza, the information processing part 55 refers to the disease table 61 and acquires the criterion (B) as the facility alarm criterion 61*c* corresponding to the disease type 61*a*, "influenza." Criterion (b), for example, includes two criteria. The first criterion is "the number of positive detections in the most recent single day is five or more" in step S105*a*, and the second criterion is that "the number of positive detections in the last two weeks is 10 or more" in step S105*b*. In a certain medical facility, when the disease occurrence status indicated by the aggregate information satisfies at least one of the two criteria, the alarm flag of step S106 is generated for that medical facility. Step S106 corresponds to step S6 in FIG. 3A.

Step S107 corresponds to step S7 in FIG. 3A. Based on the fact that the disease type is influenza, the information processing part 55 refers to the disease table 61 and acquires the condition (A) as the notification condition 61e corresponding to the disease type 61a, "influenza." For example, the necessity of notification of facility alarm information is set as the notification condition (A).

Step S108 corresponds to step S8 in FIG. 3A. When the information processing part 55 determines that it is necessary to notify the facility alarm information based on condition (A), the notification part 57 sends the facility alarm information. Upon notification, based on the fact that the disease type is influenza and the type of alarm information is facility alarm information, the information processing part 55 refers to the disease table 61, and acquires the method (a) as the notification method 168 for the facility alarm information of influenza. The method (a) is, for example, the setting of the contents described in the step S108 of FIG. 4A. The notification part 57 communicates the facility alarm information according to the acquired method (a). That is, the notification part 57 communicates the facility alarm information to each medical facility in the jurisdictional area by e-mail or the like, and displays the facility alarm information on a map on the web.

Figure 5A:
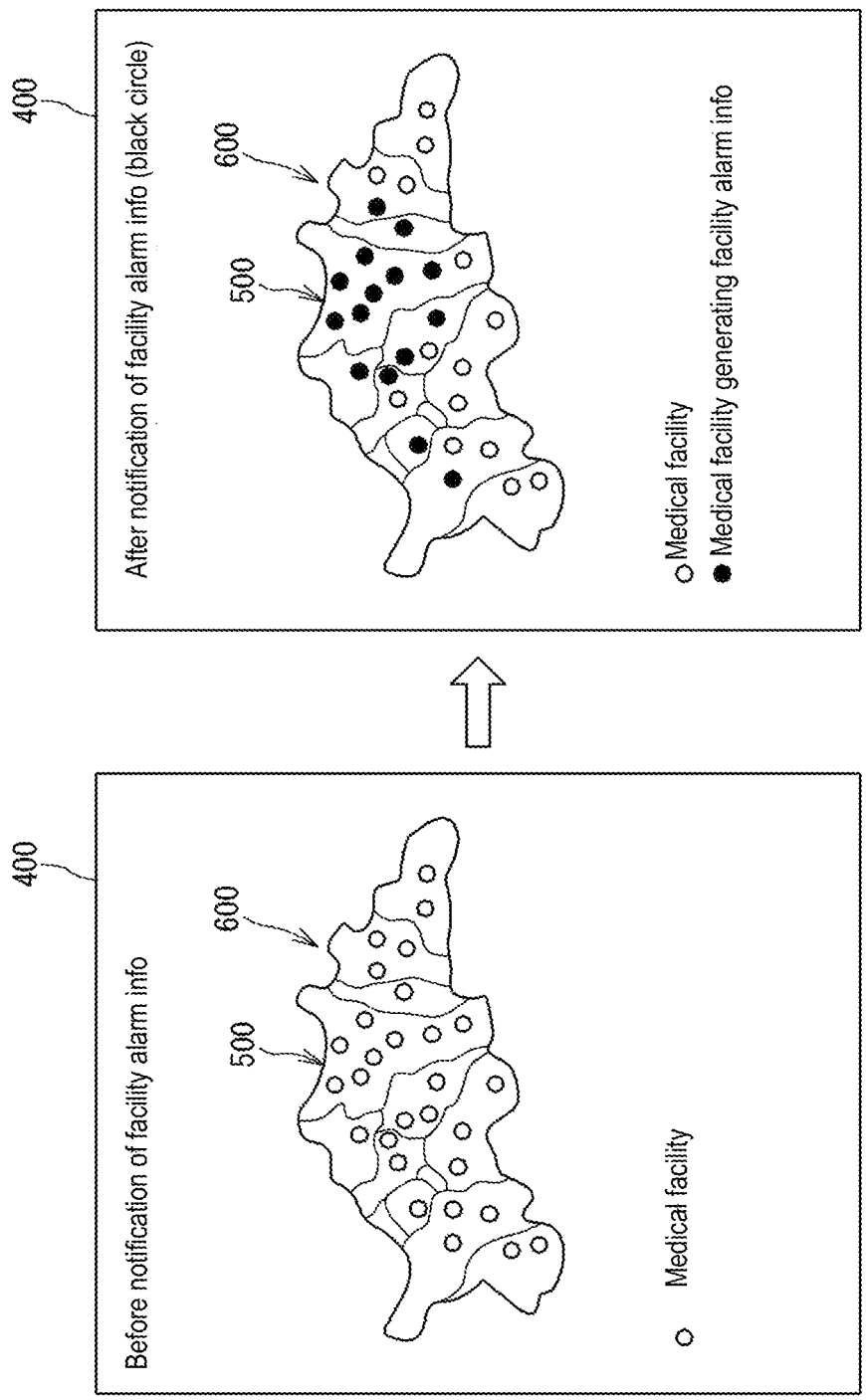
FIG. 5A is a diagram showing an example of a screen display of facility alarm information.

FIG. 5A shows an example of "display facility alarm information on a map on the Web" in step S108 of FIG. 4A. As shown in FIG. 5A, the facility alarm information displayed on the web screen 400 includes map information 600 relating to the disease occurrence status of the medical facility. The map information 600 includes a map showing the jurisdiction area 500 by the information processing apparatus 10, and information indicating the position of the medical facility in the jurisdiction area 500. In the map information 600 displayed on the screen 400, the inside of the jurisdiction area 500 is divided by municipalities, which are large area divisions for influenza in the case of influenza. The displayed jurisdiction area 500 may be divided by small area divisions.

In FIG. 5A, a circle indicates a medical facility. A white circle indicates a medical facility where facility alarm information is not generated, and a solid circle indicates a medical facility where facility alarm information is generated. It is possible to visually grasp the position of the medical facility where the facility alarm information is generated since the medical facility is shown in the map.

As shown in FIG. 5A, the notification part 57 functioning as a Web server and visually indicates the medical facility where the facility alarm information is generated by the notification process of step S108 in FIG. 4A by a black circle (the color is not particularly limited). By distinguishing and displaying the medical facilities by the presence or absence of the facility alarm information, it is possible to easily grasp the occurrence of influenza in the jurisdiction area 500.

The display shown in FIG. 5A also may be used for displaying facility alarm information for diseases other than influenza.

6.1.2 Influenza: Small Area Alarm

FIG. 3B shows the small area alarm generation process 55b for influenza. Step S109 corresponds to step S9 in FIG. 3B. Based on the fact that the disease type is influenza, the information processing part 55 refers to the disease table 61 and selects school district as the small area division 161 corresponding to the disease type 61a, "influenza."

Step S110 corresponds to step S10 in FIG. 3B. The information processing part 55 monitors the number of medical facilities with an alarm flag set for each school district.

Step S111 corresponds to step S11 in FIG. 3B. Based on the fact that the disease type is influenza, the information processing part 55 refers to the disease table 61 and acquires the criterion (C) as the small area alarm criterion 162 set according to the selected school district. The criterion (C) is, for example, "the number of alarm flags in the last two weeks is three or more."

Step S112 corresponds to step S12 in FIG. 3B. When the number of alarm flags of a school district satisfies criterion (C), the information processing part 55 generates small area alarm information corresponding to the school district.

Step S113 corresponds to step S13 in FIG. 3B. The notification part 57 communicates the small area alarm information. Upon notification, based on the fact that the disease type is influenza and the type of alarm information type is small area alarm information, the information processing part 55 refers to the disease table 61, and acquires the method (b) as the notification method 169 for the small area alarm information of influenza. The method (b) is, for example, the setting of the contents described in the step S113 of FIG. 4B. The notification part 57 communicates the small area alarm information according to the acquired method (b). That is, the notification part 57 communicates information indicating that influenza is spreading within the school district as a warning report by e-mail or the like to the school and the medical facility in the corresponding school district, and contacts each medical institution located outside the corresponding school district by e-mail. The notification part 57 also displays the area indicating the school district on a map on the Web.

Figure 4B:
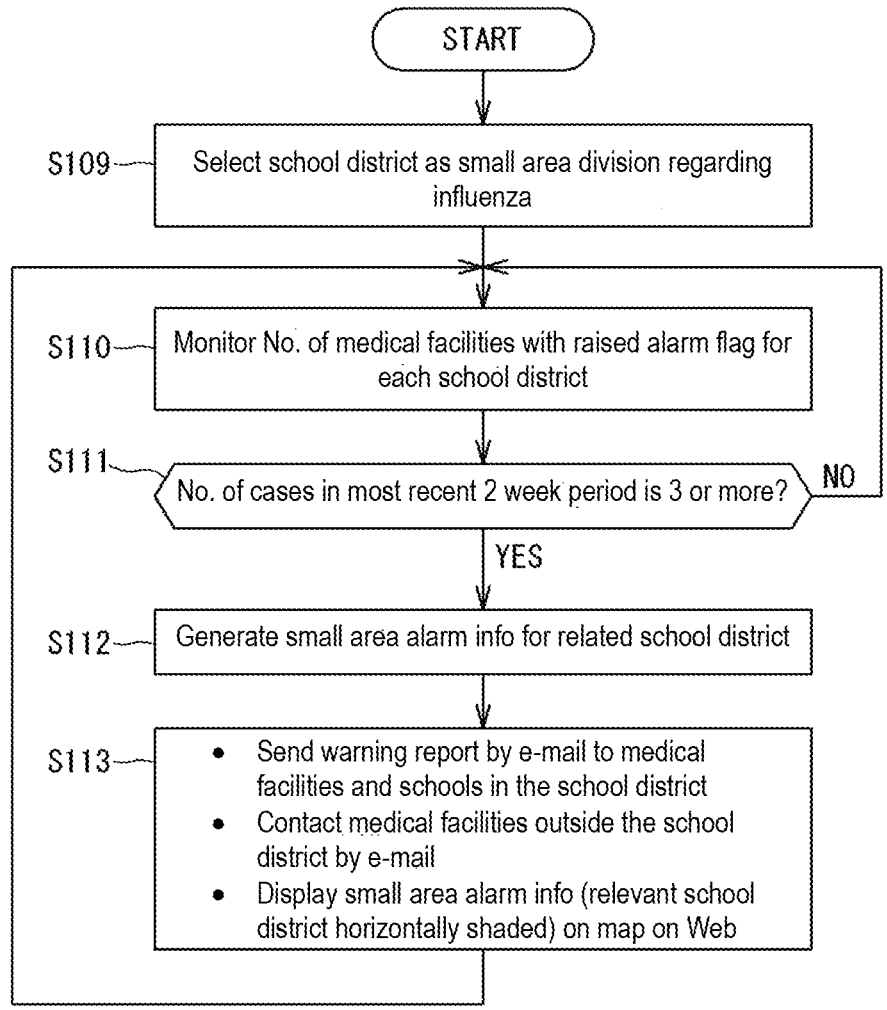
FIG. 4B is a flowchart of the small area alarm generation process for influenza.
Figure 5B:
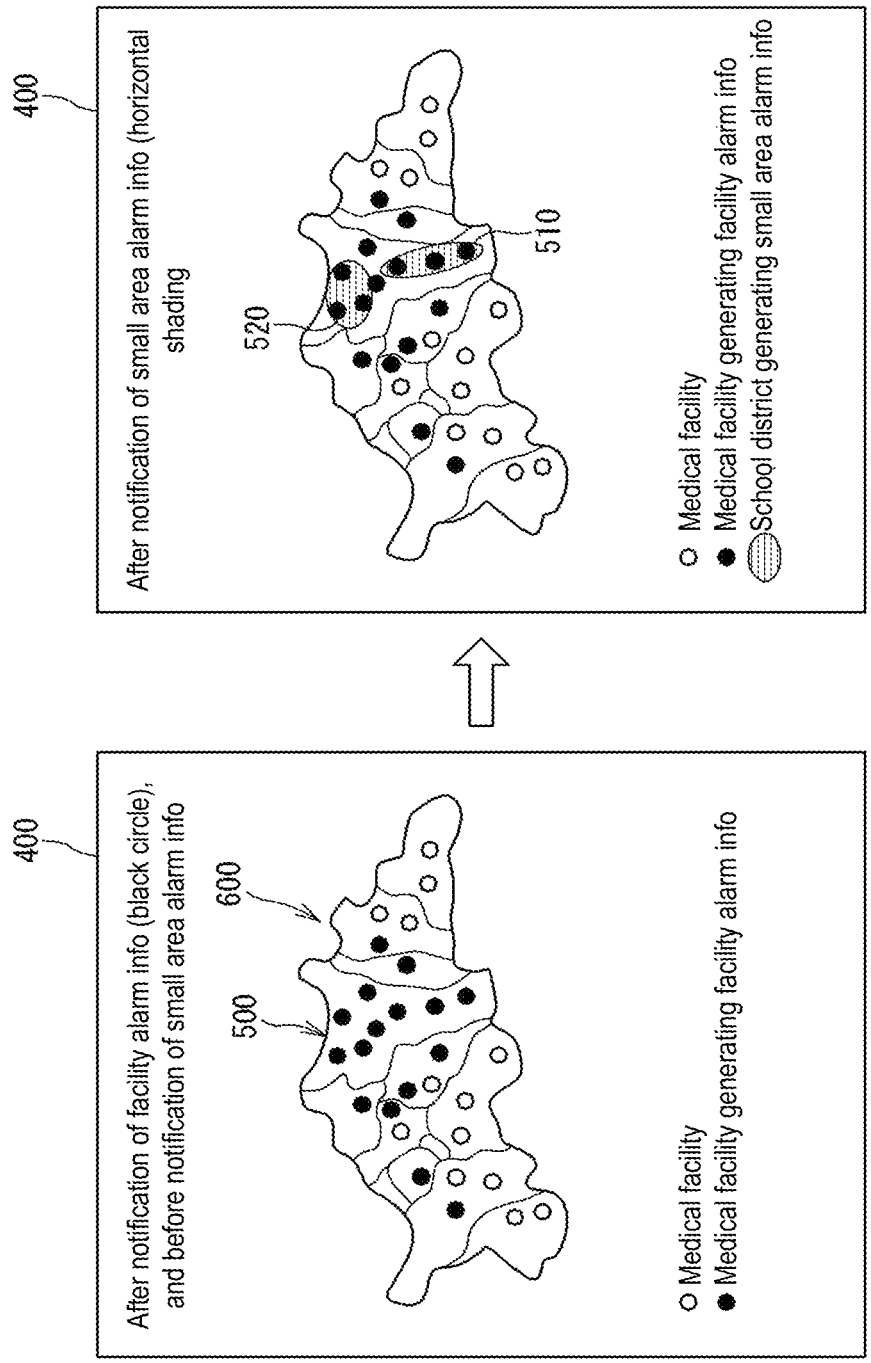
FIG. 5B is a diagram showing an example of a screen display of small area alarm information.

FIG. 5B shows an example of "display small area alarm information (horizontal shaded to indicate the school district) on the map on the Web" in step S113 of FIG. 4B. As shown in FIG. 5B, when the small area alarm information is communicated, the display on the Web screen 400 shows the school districts 510 and 520 where the small area alarm information is generated. In FIG. 5B, horizontal lines indicate the school districts 510 and 520. By displaying the school districts 510 and 520 in which the small area alarm information is generated in a manner distinguished from the areas where the small area alarm information is not generated, it is possible to easily grasp the occurrence status of influenza in the jurisdiction area 500. That is, it is possible to grasp the extent to which the influenza is spreading more accurately. In particular, if the small area division is a school district, the display in FIG. 5B is useful for the school.

Figure 5C:
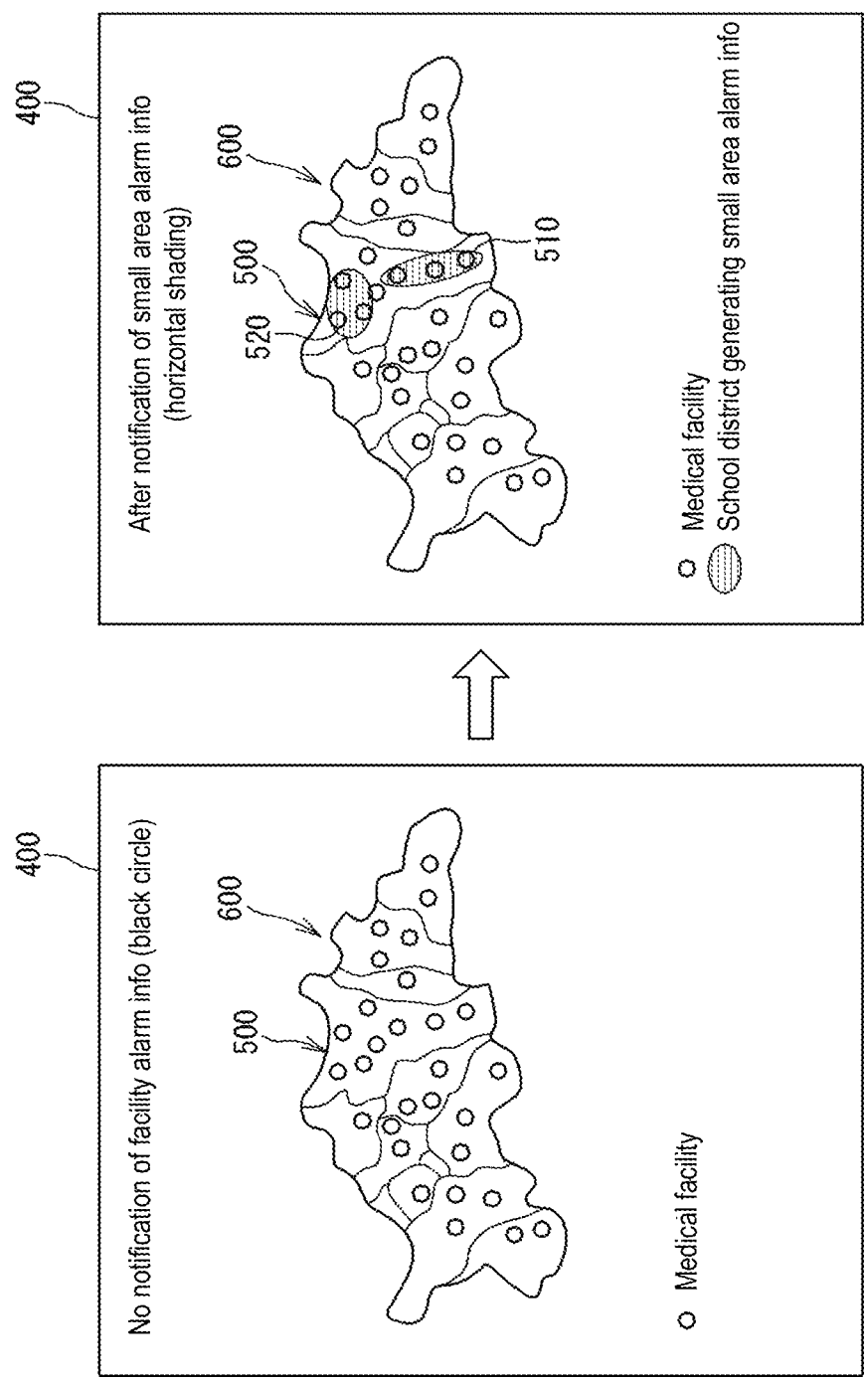
FIG. 5C is a diagram showing an example of a screen display of small area alarm information.

When displaying the school districts 510 and 520 in which the small area alarm information is generated on the Web screen 400, as shown in FIG. 5C, only the small area alarm information may be displayed without displaying the black circle indicating the facility alarm information.

The display shown in FIG. 5B also may be used for displaying facility alarm information for diseases other than influenza.

6.1.3 Influenza: Large Area Alarm

Figure 4C:
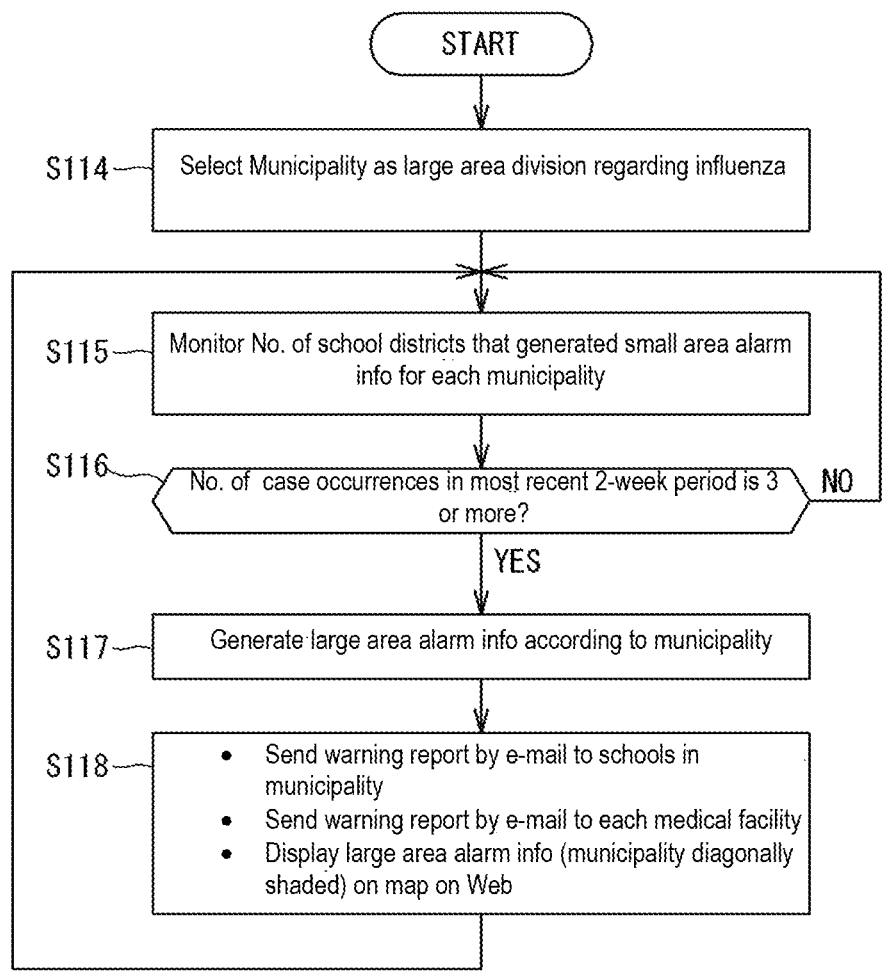
FIG. 4C is a flowchart of the large area alarm generation process for influenza.

FIG. 4C shows the large area alarm generating process 55c for influenza. Step S114 corresponds to step S14 of FIG. 3C. Based on the fact that the disease type is influenza, the information processing part 55 refers to the disease table 61 and selects municipality as the large area division 163 corresponding to the disease type 61a, "influenza."

Step S115 corresponds to step S15 in FIG. 3C. The information processing part 55 monitors each municipality in which the small area alarm information is generated for each municipality.

Step S116 corresponds to step S16 in FIG. 3C. Based on the fact that the disease type is influenza, the information processing part 55 refers to the disease table 61 and acquires the criterion (D) as the large area alarm criterion set according to the selected municipality. Criterion (D) is, for example, "the number of small area alarm information of the last two weeks is three or more."

Step S117 corresponds to step S17 in FIG. 3C. When the number of small area alarm information in a city satisfies criterion (D), the information processing part 55 generates large area alarm information corresponding to the city.

Step S118 corresponds to step S18 in FIG. 3C. The notification part 57 communicates the small area alarm information. Upon notification, based on the fact that the disease type is influenza and the type of alarm information type is large area alarm information, the information processing part 55 refers to the disease table 61, and acquires the method (c) as the notification method 170 for the large area alarm information of influenza. The method (c) is, for example, the setting of the contents described in the step S118 of FIG. 4C. The notification part 57 communicates the small area alarm information according to the acquired method (c). That is, the notification part 57 communicates information warning that the influenza is spreading in the relevant municipality as a warning report by e-mail or the like to the school in the relevant municipality, and also notifies each medical facility in the jurisdictional area by e-mail or the like. The notification part 57 also displays the area indicating the school district on a map on the Web.

Figure 5D:
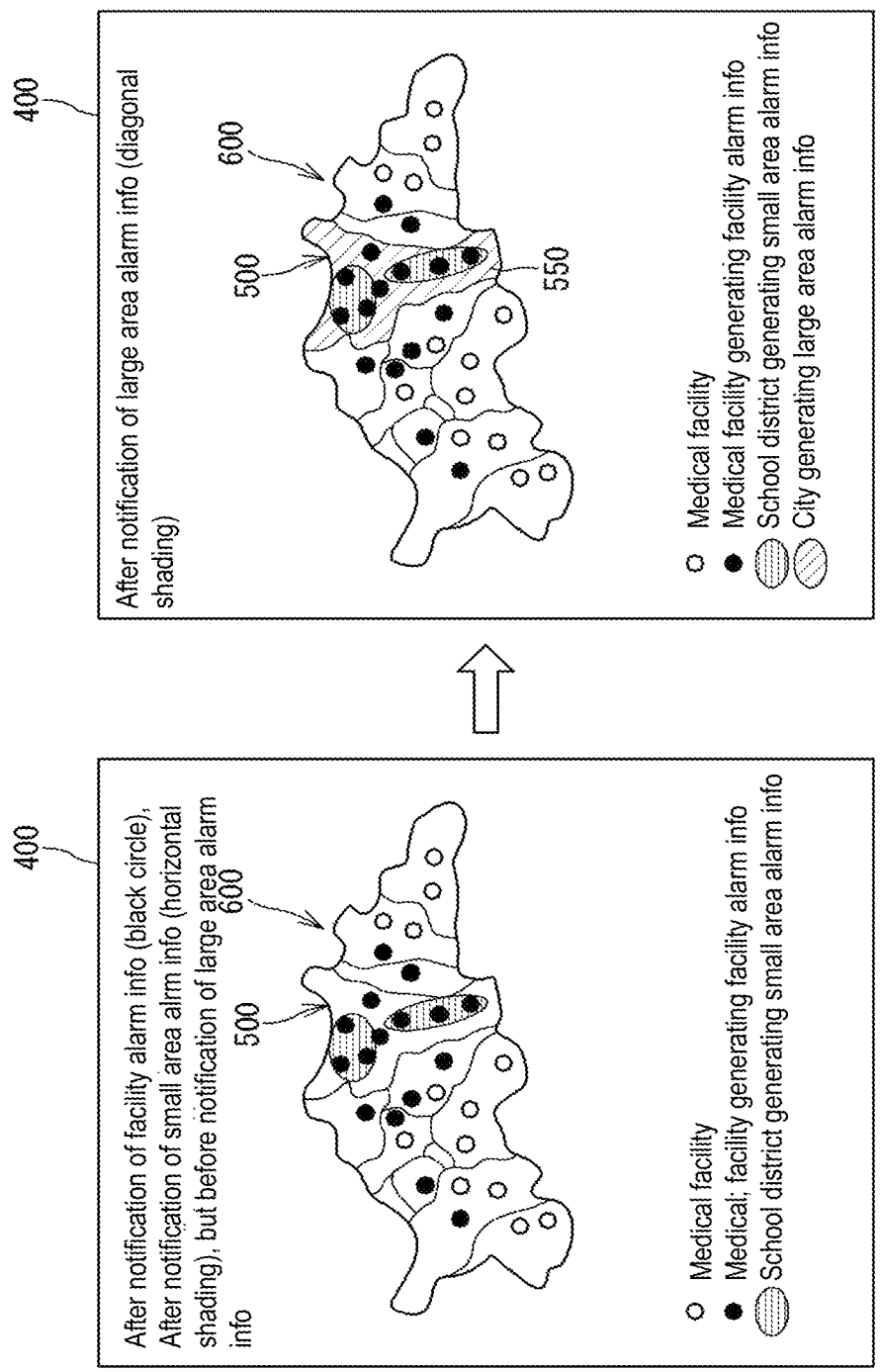
FIG. 5D is a diagram showing an example of a screen display of large area alarm information.

FIG. 5D shows an example of "display large area alarm information (diagonally shaded for relevant municipalities)" on the map on the Web in step S 118 of FIG. 4C. As shown in FIG. 5D, when the large area alarm information is communicated, the display on the Web screen 400 shows the city 550 where the large area alarm information is generated. In FIG. 5D, the shaded area 550 is diagonally shaded. By displaying the city 550 in which the large area alarm information is generated in a manner distinguished from the areas where the large area alarm information is not generated, it is possible to easily grasp the occurrence status of influenza in the jurisdiction area 500. That is, it is possible to grasp the extent to which the influenza is spreading more accurately. In particular, if the large area division is a municipality, the display of FIG. 5D is useful for facilities such as schools in the municipality.

Since the small area alarm information and the large area alarm information are both displayed on the screen 400 of FIG. 5D, it is possible to easily grasp in which school district in the city the influenza is generated.

Figure 5E:
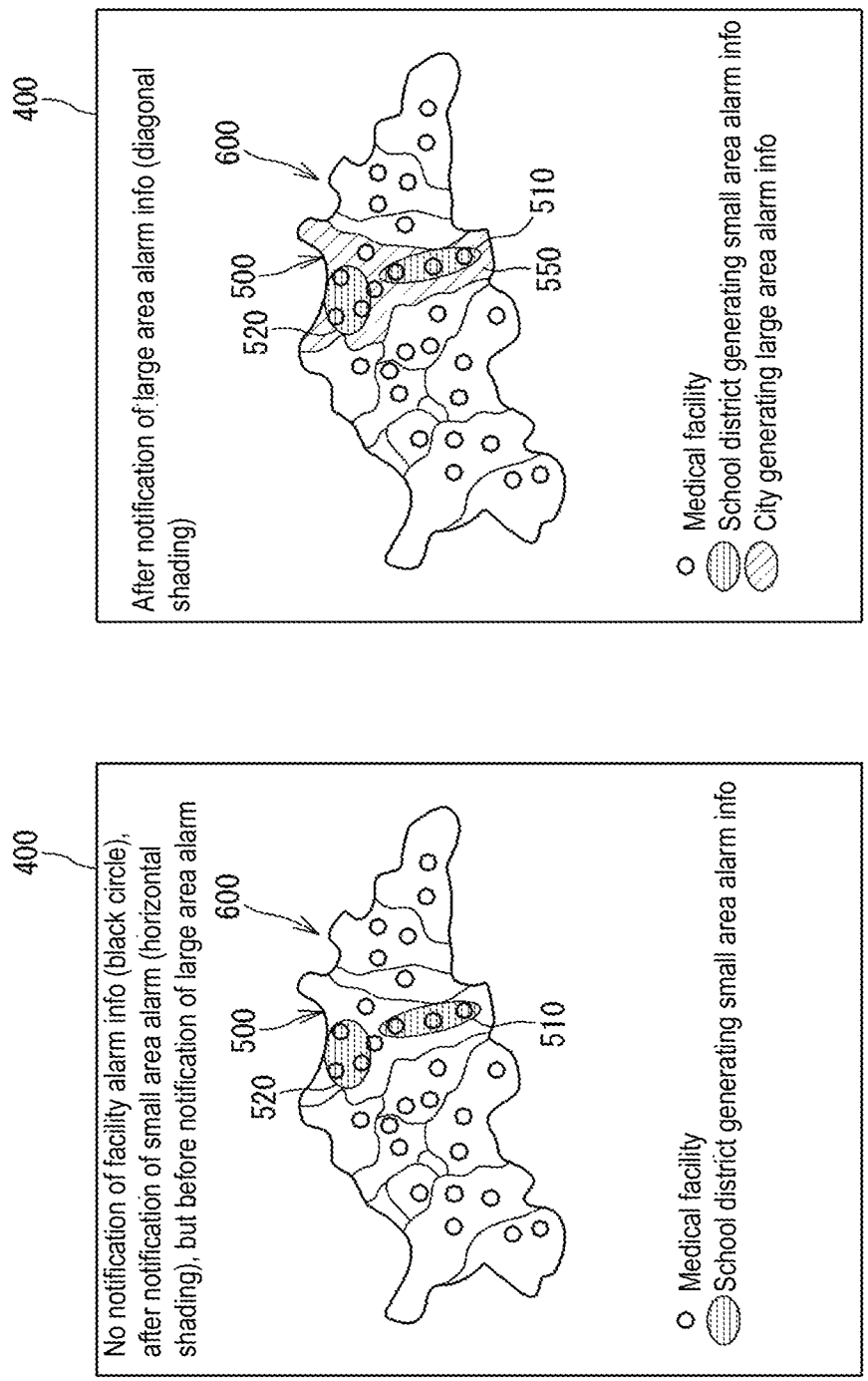
FIG. 5E is a diagram showing an example of a screen display of large area alarm information.

When displaying the city 550 in which the large area alarm information is generated on the Web screen 400, as shown in FIG. 5E, only the small area alarm information and large area alarm information may be displayed without displaying the black circle indicating the facility alarm information.

The displays shown in FIGS. 5D and 5E also may be used for displaying facility alarm information for diseases other than influenza.

6.2 Rubella

Figure 6A:
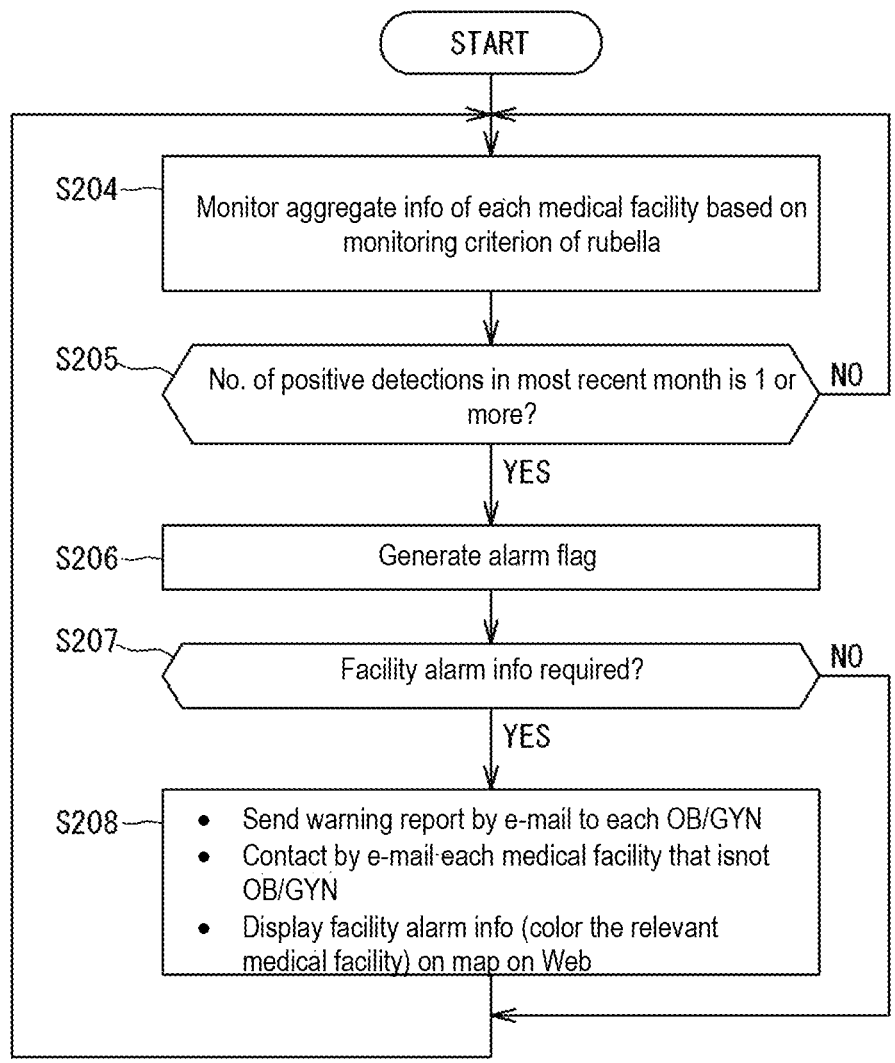
FIG. 6A is a flowchart of the facility alarm generation process for influenza for rubella.

FIG. 6A shows the facility alarm generation process 55a for rubella. Steps S204 to S208 correspond to step S4 to step S8 in FIG. 3A. In the case of rubella, the facility alarm criterion is, for example, "the number of positive detections in the most recent one month is one or more" as shown in step S205.

The method for communicating the facility alarm information of rubella is, for example, as described in step S208 of FIG. 6A. As the notification method of alarm information can be set differently for each disease type, an appropriate notification method can be set according to the disease type.

Figure 6B:
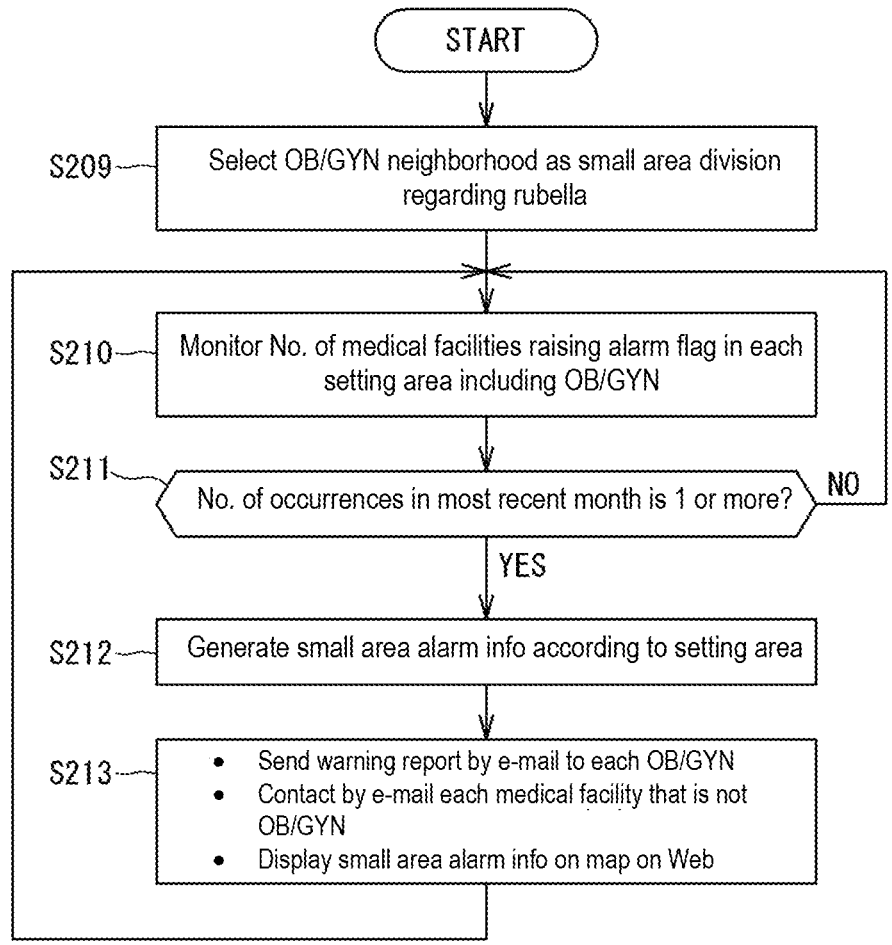
FIG. 6B is a flowchart of the small area alarm generation process for rubella.

FIG. 6B shows the small area alarm generation process 55b for rubella. Steps S209 to S213 correspond to step S9 to step S13 in FIG. 3B. In rubella, for example, as shown in step S209, "neighborhood of obstetrics and gynecology" is selected as the small area division.

In the case of rubella, the small area alarm criterion is, for example, "the number of alarm flags of the most recent one month is one or more" as shown in step S211.

The method for communicating the facility alarm information of rubella is, for example, as described in step S213 of FIG. 6B. With regard to rubella, although it is unnecessary to generate large area alarm information in order to notify each gynecology department within the jurisdictional area with alarms with one or more positive detections, generation of large area alarm information for rubella may be generated.

Here, for the points not described with reference to FIG. 6A and FIG. 6B, instances where "influenza" appears in the explanation of FIGS. 4A and 4B may be replaced with "rubella" and are cited as an explanation of FIGS. 6A and 6B.

6.3 Dengue Fever

Figure 7A:
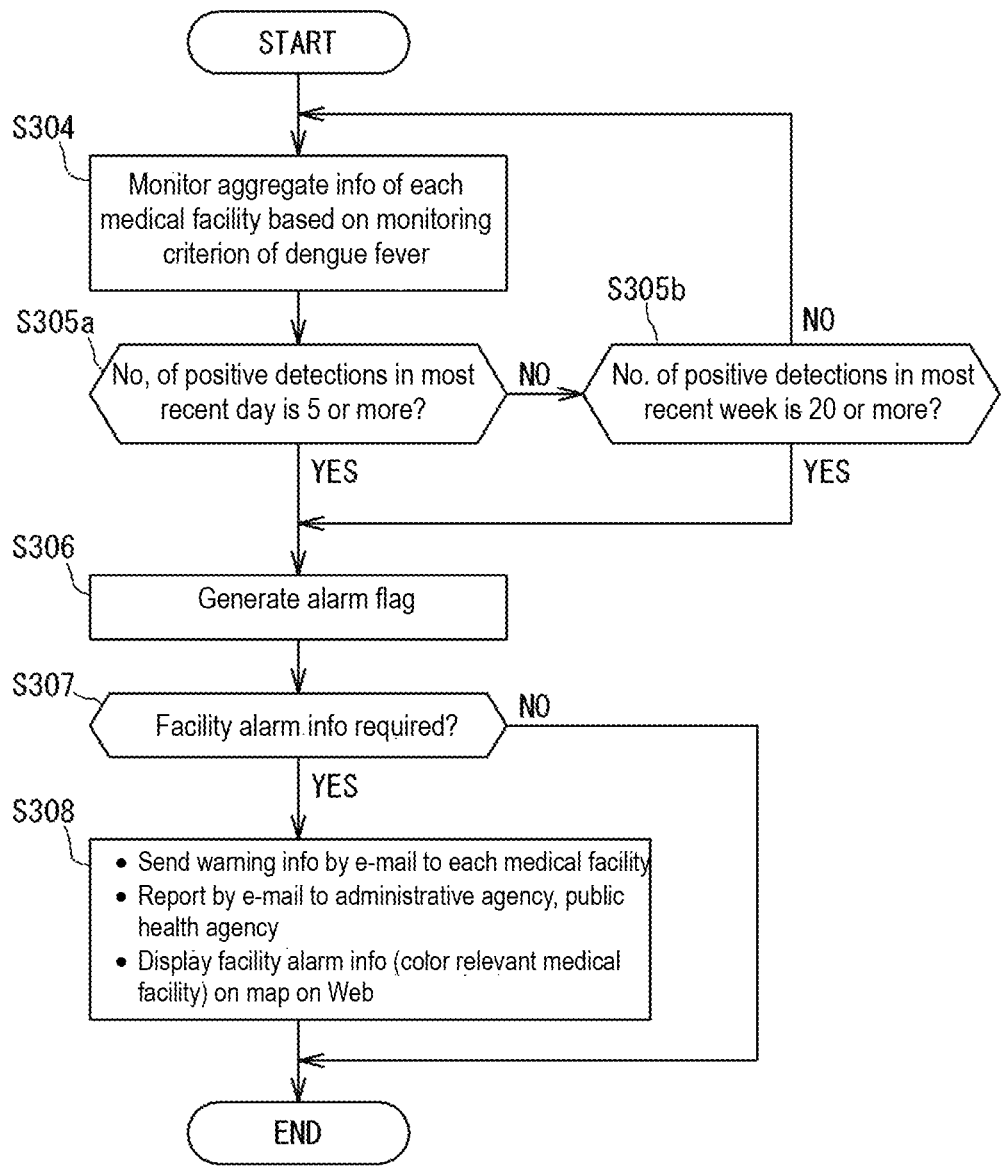
FIG. 7A is a flowchart of the facility alarm generation process for dengue fever.

FIG. 7A shows the facility alarm generation process 55a for dengue fever. Steps S304 to S308 respectively correspond to step S4 to step S8 in FIG. 3A. Note that steps S305a and S305b correspond to step S5 of FIG. 3A.

The facility alarm criteria relating to dengue fever includes, for example, two criteria. The first criterion is "the number of positive detections in the most recent single day is five or more" in step S305a, and the second criterion is "the number of positive detections in the last two weeks is 20 or more" in step S305b. In a certain medical facility, when the disease occurrence status indicated by the aggregate information satisfies at least one of the two criteria, the alarm flag for that medical facility is generated.

The method for communicating the facility alarm information of dengue fever is, for example, as described in step S308 of FIG. 7A.

Figure 7B:
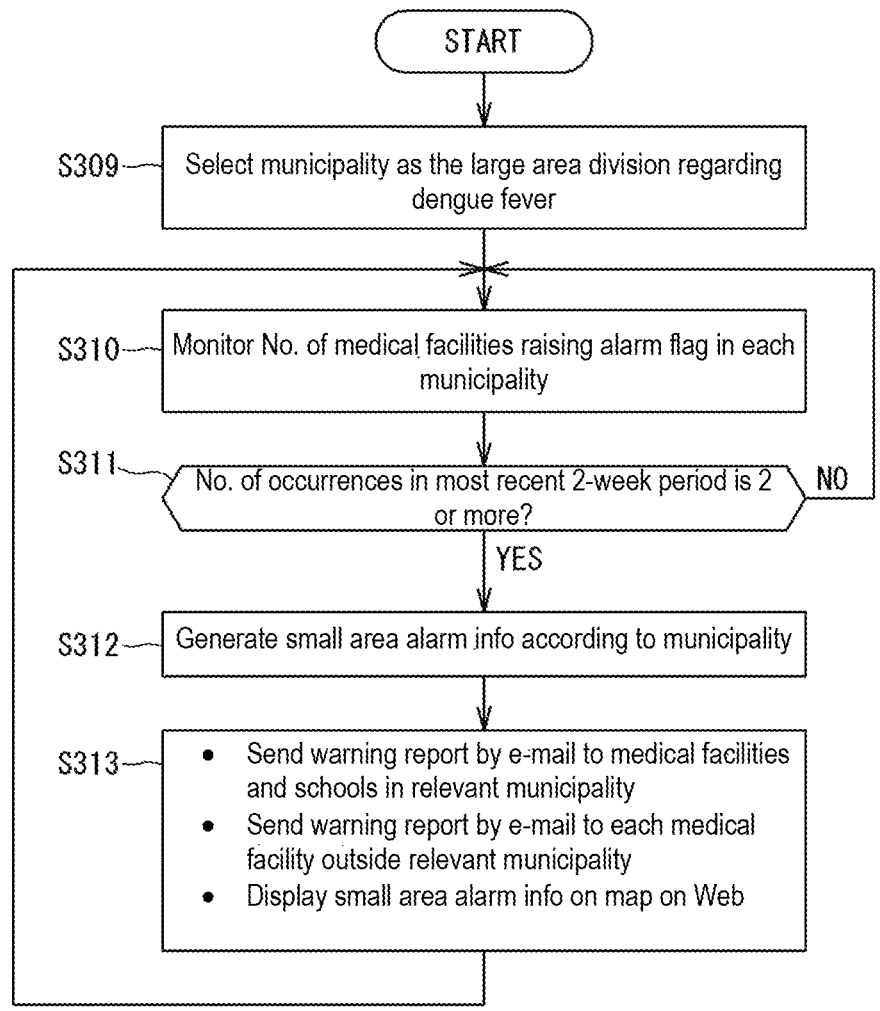
FIG. 7B is a flowchart of the small area alarm generation process for dengue fever.

FIG. 7B shows the small area alarm generation process 55b for dengue fever. Steps S309 to S313 correspond to step S9 to step S13 in FIG. 3B. In dengue fever, for example, a municipality is selected as a small area division, as shown in step S309.

In the case of dengue fever, the small area alarm criterion is, for example, "the number of alarm flags of the most recent two weeks is one or more" as shown in step S311.

The method for communicating the facility alarm information of dengue fever is, for example, as described in step S313 of FIG. 7B.

Figure 7C:
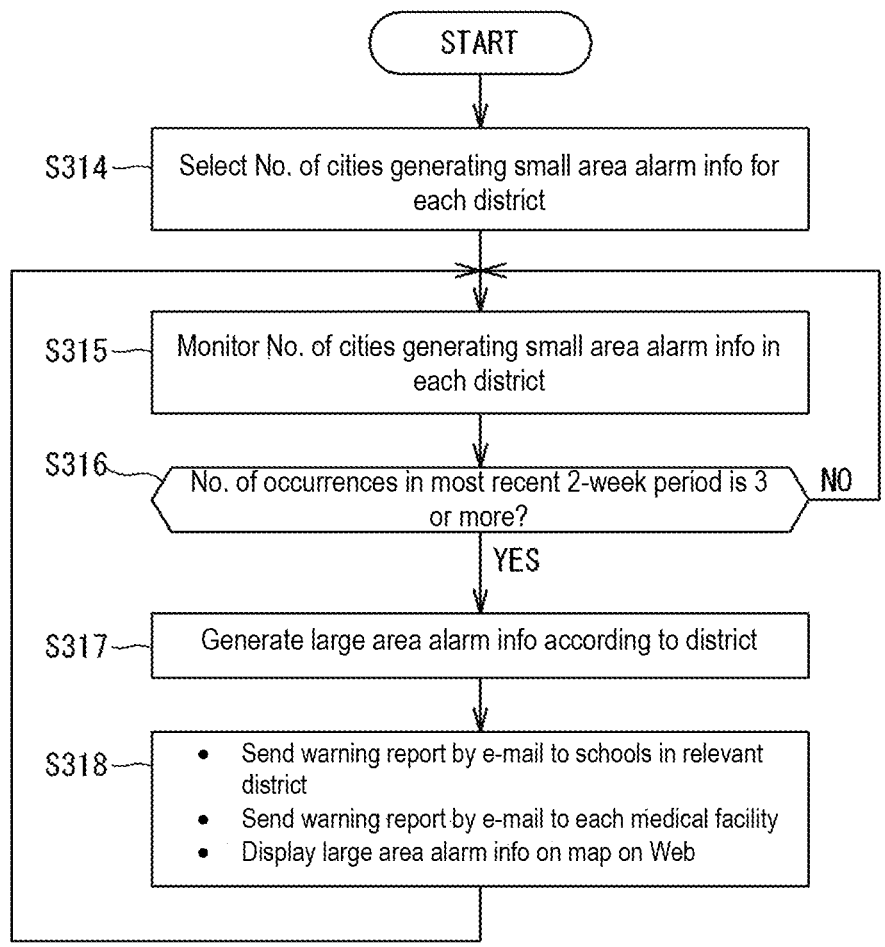
FIG. 7C is a flowchart of the large area alarm generation process for dengue fever.

FIG. 7C shows the large area alarm generating process 55c for dengue fever. Steps S314 to S218 respectively correspond to step S14 to step S18 in FIG. 3C.

In dengue fever, for example, "district" is selected as a small area division, as shown in step S314. In dengue fever, the large area alarm criterion is, for example, as shown in step S316, "the number of small area alarm information of the last two weeks is three or more." The method for communicating the facility alarm information of dengue fever is, for example, as described in step S318 of FIG. 7C.

That is, an alarm is communicated to schools in the relevant district by e-mail or the like, an alarm is communicated by e-mail or the like to each medical facility in the jurisdictional area, and an area showing the district is displayed on the map on the web.

Here, for the points not described in FIGS. 7A, 7B, and 7C, instances where "influenza" appears in the explanation of FIGS. 4A, 4B, and 4C may be replaced with "dengue fever" and are cited as an explanation of FIGS. 7A, 7B, and 7C.

6.4 Drug Resistant Bacteria

Figure 8A:
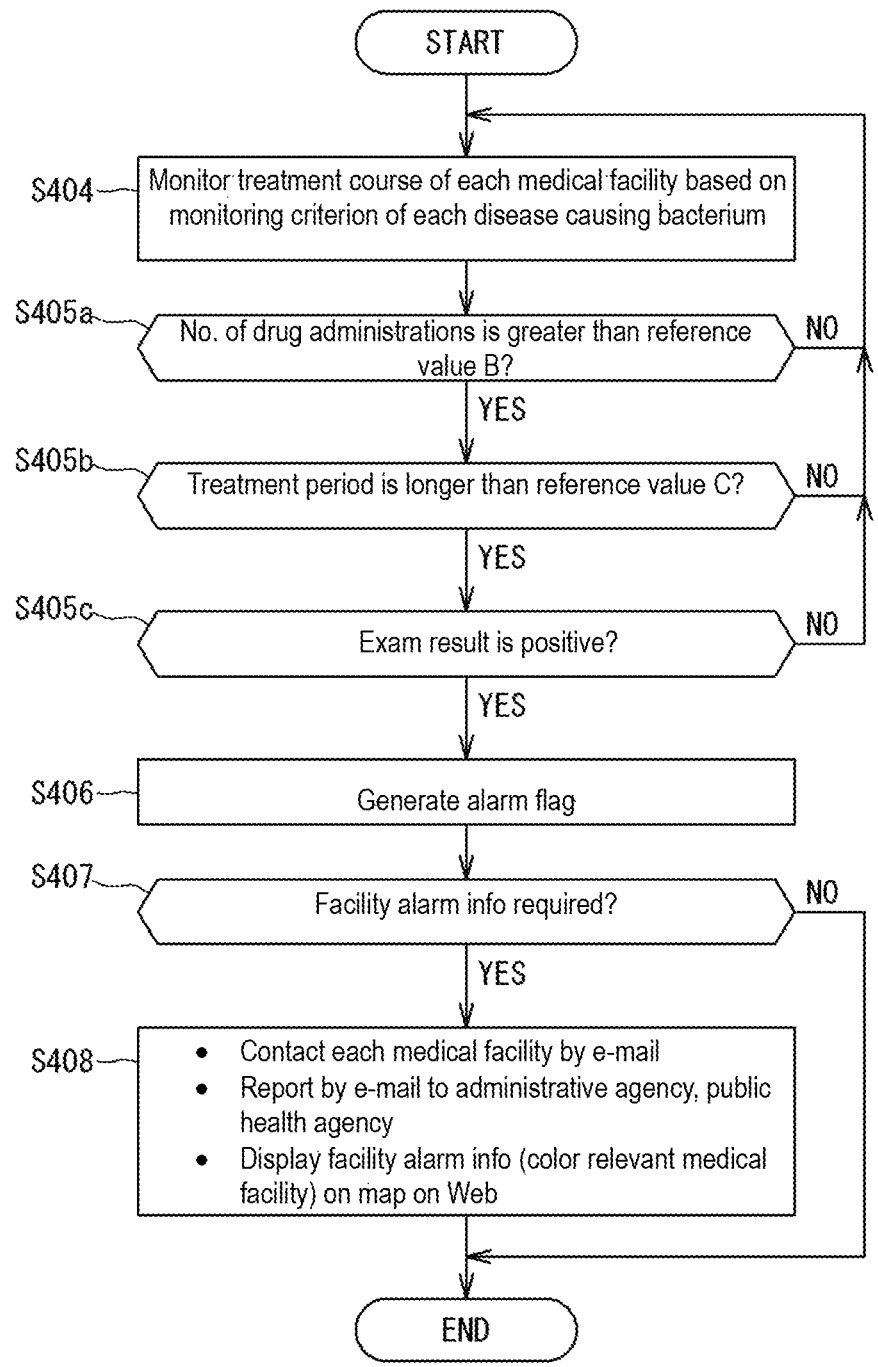
FIG. 8A is a flowchart of the facility alarm generation process for drug resistant bacteria.

FIG. 8A shows a facility alarm generation process 55a for infection by drug resistant bacteria. Steps S404 to S408 respectively correspond to step S4 to step S8 in FIG. 3A. Note that steps S405a to S405c correspond to step S3 of FIG. 3A.

In order to detect the occurrence of drug-resistant bacteria, treatment information including progress information as well as the result of treatment is used as disease information. In step S404, aggregate information on the treatment course relating to *Staphylococcus aureus* shown in FIG. 2C is monitored.

Facility alarm criteria for drug-resistant bacteria include, for example, three criteria. The first criterion is "the number of drug doses is equal to or larger than a reference value" in step S405a, the second criterion is "the treatment period is equal to or longer than the reference value" in step S405b, the third criterion is "the test result is positive" in S405c. In a certain medical facility, when the disease occurrence status indicated by the aggregate information satisfies all three criteria, the alarm flag for that medical facility is generated.

The method for communicating the facility alarm information of drug resistant bacteria is, for example, as described in step S408 of FIG. 8A.

Figure 8B:
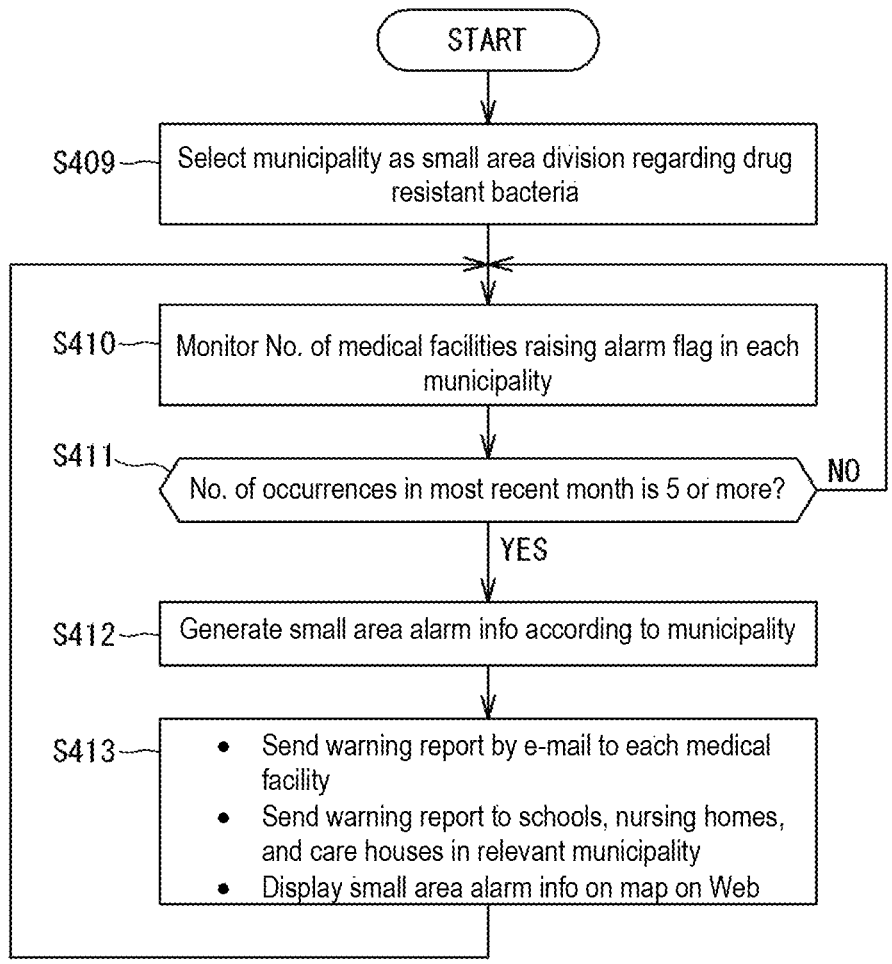
FIG. 8B is a flowchart of the small area alarm generation process for drug resistant bacteria.

FIG. 8B shows the small area alarm generation process 55b for drug resistant bacteria. Steps S409 to S413 respectively correspond to step S9 to step S13 in FIG. 3B. In drug resistant bacteria, for example, a municipality is selected as a small area division, as shown in step S409.

In the drug resistant bacteria, the small area alarm criterion is, for example, "the number of alarm flags of the most recent one month is five or more" as shown in step 411.

The method for communicating the facility alarm information of drug resistant bacteria is, for example, as described in step S413 of FIG. 8B. That is, a warning report is communicated to each medical facility in the jurisdictional area by e-mail or the like, a warning is communicated to the schools, a nursing homes and a care houses in the municipality, and the area representing the municipality is indicated in the map on the web.

Figure 8C:
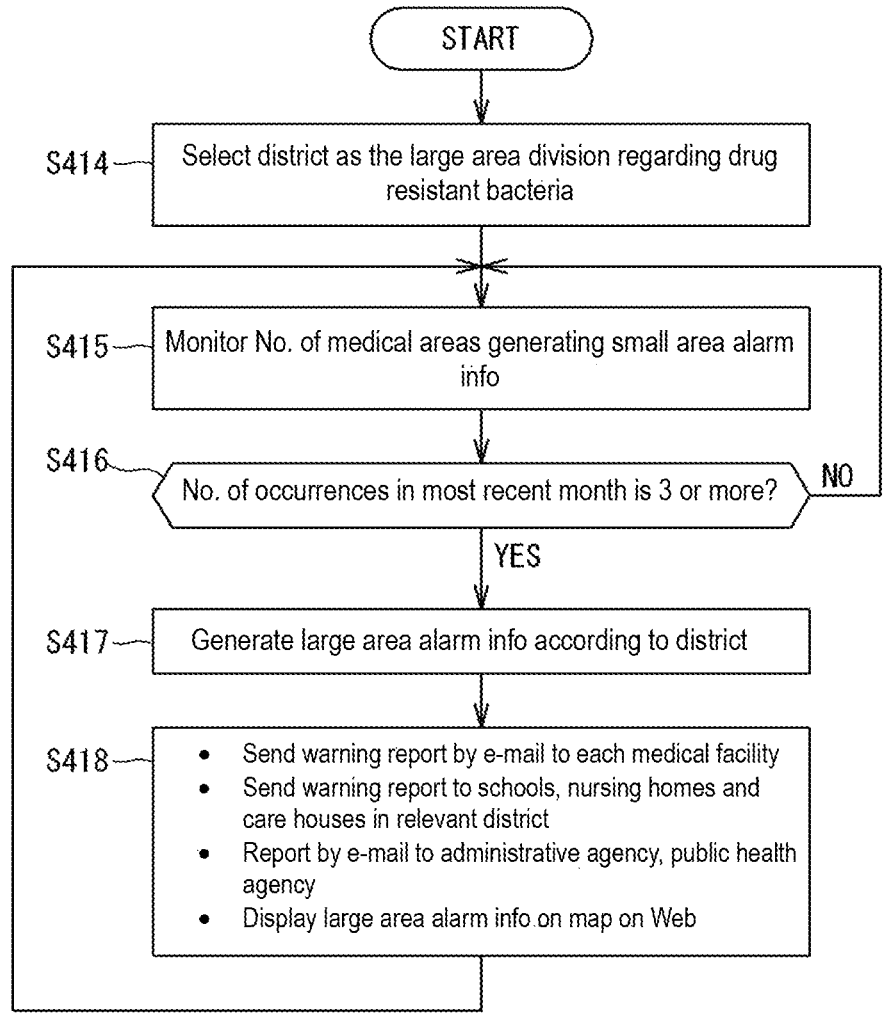
FIG. 8C is a flowchart of the large area alarm generation process for drug resistant bacteria.

FIG. 8C shows the large area alarm generation process 55c for drug resistant bacteria. Steps S344 to S248 respectively correspond to step S14 to step S18 in FIG. 3C.

In drug resistant bacteria, for example, a "district is selected as a large area division, as shown in step S414. The large area alarm criterion is, for example, as shown in step S416, "the number of small area alarm information of the last month is three or more." The method for communicating the facility alarm information of drug resistant bacteria is, for example, as described in step S418 of FIG. 8C.

Here, for the points not described in FIGS. 8A, 8B, and 8C, instances where "influenza" appears in the explanation of FIGS. 4A, 4B, and 4C may be replaced with "drug resistant bacteria" and are cited as an explanation of FIGS. 8A, 8B, and 8C.

Note that although in the present embodiment the information processing unit 55 refers to the disease table 61 on the basis of the disease type to be monitored, and selects the facility alarm criterion, small area division, large area division, notification method and the like according to the disease type, the invention is not limited to this arrangement. For example, a list of disease types (influenza, rubella and the like), a list of small area divisions (school districts, municipalities and the like), and a list of notification methods may be recorded in advance in the storage device 60 using an input device, and the user may select a specific disease type, small area division, notification method and the like from the lists via the input device.

What is claimed is:

1. A method for monitoring infectious disease, the method comprising:

executing by a first computer, wherein the first computer comprises a processor executing a program stored in a non-transitory computer-readable memory, the program configuring the first computer to perform operations, comprising:

connecting the first computer to a network to obtain disease information from each respective second computers located in a plurality of medical facilities through the network;

determining by the first computer, medical facilities which are associated with a first zone where a particular disease occurs, based on the obtained disease information and a first criterion related to a disease occurrence status at the medical facilities;

counting by the first computer, the determined medical facilities which are associated with the first zone; and generating by the first computer, first area alarm information related to the disease occurrence status in the first zone based on the counting result and a second criterion related to the disease occurrence status in the first zone.

2. The monitoring method of claim 1, wherein a first area division for partitioning the first zone is selected from district, prefecture, municipality, county, school district, or area.

3. The monitoring method according to claim 1, wherein a first area division for partitioning the first zone is selected from a plurality of types of area divisions.

4. The monitoring method according to claim 3, wherein the first area division is selected based on a disease type.

5. The monitoring method according to claim 3, wherein the second criterion is a criterion according to a type of the first area division.

6. The monitoring method according to claim 3, further comprising:

communicating, by the first computer, a notification of the first area alarm information by a notification method according to a type of the first area division.

7. The monitoring method according to claim 6, wherein a destination of the notification is a facility other than a medical facility.

8. The monitoring method according to claim 6, wherein the notification of the first area alarm information is displayed on a screen of a display device so as to distinguish between a first zone that has generated first area alarm information and a first zone that has not generated first area alarm information in the screen, wherein a plurality of the medical facilities are displayed on a map in the screen.

9. The monitoring method according to claim 1, further comprising:

communicating, by the first computer, a notification of facility alarm information of medical facilities generated based on the disease occurrence status for each medical facility.

10. The monitoring method according to claim 9, wherein the notification of the facility alarm information of the medical facility is displayed on a screen of a display device so as to distinguish between the medical facilities for which the facility alarm information was generated and medical facilities for which the facility alarm information was not generated in the screen, wherein a plurality of the medical facilities are displayed on a map in the screen.

11. The monitoring method according to claim 1, further comprising:
generating, by the first computer, second area alarm information relating to a disease occurrence status in a second zone based on a disease occurrence situation in the second zone partitioned by a second area division of a type different from the first area division and a third criterion related to a disease occurrence status in the second zone.

12. The monitoring method according to claim 11, wherein the second area division is selected based on a disease type.

13. The monitoring method according to claim 11, wherein the third criterion is a criterion according to the type of the second area division.

14. The monitoring method according to claim 11, further comprising:
communicating, by the first computer, the second area alarm information by a notification method according to the type of the second area division.

15. The monitoring method according to claim 14, wherein the notification of the second area alarm information is displayed on a screen of a display device so as to distinguish between a second zone that has generated second area alarm information and a second zone that has not generated second area alarm information in the screen, wherein a plurality of the medical facilities are displayed on a map in the screen.

16. The monitoring method according to claim 1, wherein the disease information comprises a disease type, and at least one result of a test result, a diagnosis result and a treatment result performed in a medical facility, and a date.

17. An information processing apparatus for monitoring infectious disease, comprising:
an information processing part that executes:
a process of determining medical facilities where a particular disease occurs based on disease information acquired from the medical facilities and a first criterion related to a disease occurrence status at the medical facilities;
a process of counting the determined medical facilities which are associated with a first zone; and
a process for generating first area alarm information relating to a disease occurrence status in the first zone based on the counting result and a second criterion related to the disease occurrence status in the first zone.

18. A non-transitory computer readable medium storing a computer program for enabling a computer to execute:
a process of determining medical facilities where a particular disease occurs based on disease information acquired from the medical facilities and a first criterion related to a disease occurrence status at the medical facilities;
a process of counting the determined medical facilities which are associated with a first zone partitioned by a first area division; and
a process of generating first area alarm information related to the disease occurrence status in the first zone based on the counting result and a second criterion related to the disease occurrence status in the first zone.

19. An information processing system for monitoring infectious disease, comprising:
a first information processing apparatus that executes: a process of determining medical facilities where a particular disease occurs based on disease information acquired from the medical facilities and a first criterion related to a disease occurrence status at the medical facilities;
a process of counting the determined medical facilities which are associated with a first zone partitioned by a first area division; and
a process of generating first area alarm information relating to a disease occurrence status in the first zone based on the counting result and a second criterion related to the disease occurrence status in the first zone; and
a second information processing apparatus that is separate from the first information processing apparatus, and executes a process to communicate a notification of first area alarm information provided from the first information processing apparatus by a notification method according to a type of first area division.

20. The information processing system of claim 19, wherein the first area alarm information generated by the first information processing apparatus comprises personal information;
the first information processing apparatus executes a process to provide the first area alarm information excluding the personal information to the second information processing apparatus, and a process to notify the medical facility of the first area alarm information including the personal information; and
the second information processing apparatus notifies facilities other than medical facilities of the first area alarm information that excludes the personal information.

* * * * *